Figure 1:
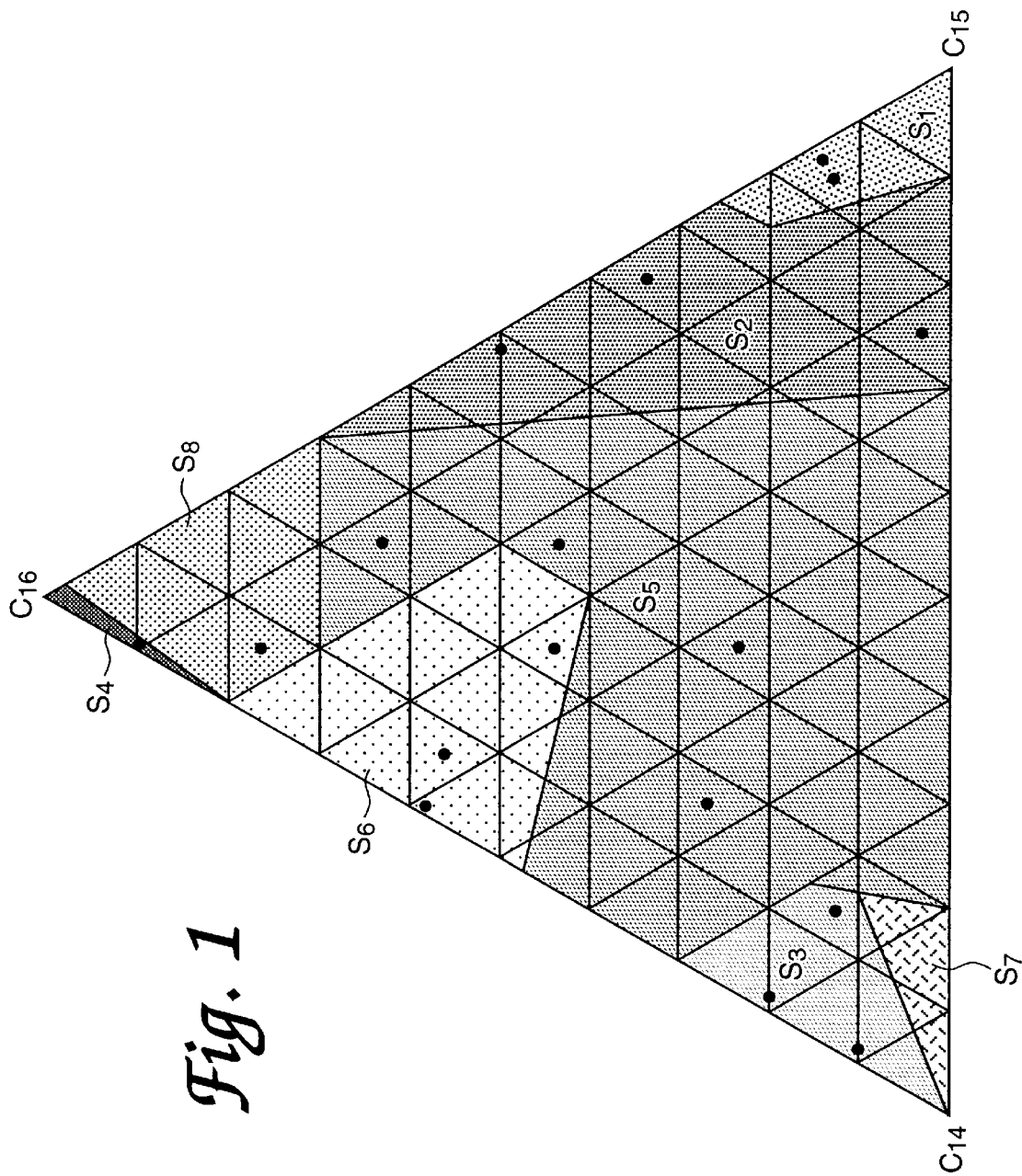

United States Patent

Haget et al.

[11] Patent Number: 5,997,762
[45] Date of Patent: Dec. 7, 1999

[54] MOLECULAR ALLOYS FOR STORING AND RESTORING THERMAL ENERGY BY PHASE CHANGE

[75] Inventors: Yvette Haget, Merignac; Denise Mondieig, Bordeaux, both of France; Miguel-Angel Cuevas-Diarte, Barcelona, Spain

[73] Assignee: Centre National de la Recherche Scienfique, Paris, France

[21] Appl. No.: 07/988,949

[22] PCT Filed: Jul. 3, 1992

[86] PCT No.: PCT/FR92/00636

§ 371 Date: May 4, 1993

§ 102(e) Date: May 4, 1993

[87] PCT Pub. No.: WO93/01250

PCT Pub. Date: Jan. 21, 1993

[30] Foreign Application Priority Data

Jul. 10, 1991 [FR] France ................... 91 08695

[51] Int. Cl.[6] ........................................... C09K 5/06
[52] U.S. Cl. .................. 252/70; 165/10; 165/104.21; 165/104.17; 524/488; 524/489
[58] Field of Search .................. 252/73, 70; 525/50, 525/185; 165/10, 10 A, 104.21, 104.17; 524/489, 488

[56] References Cited

FOREIGN PATENT DOCUMENTS

| | | |
|---|---|---|
| 0344014 | 5/1989 | European Pat. Off. . |
| 0344014 | 11/1989 | European Pat. Off. . |
| 0412021 | 8/1990 | European Pat. Off. . |
| 0412021 | 2/1991 | European Pat. Off. . |
| 2369529 | 5/1978 | France . |
| 0022717 | 1/1981 | France . |
| 0284695 | 10/1988 | France . |
| 3141191 | 10/1981 | Germany . |
| 3141191 | 5/1983 | Germany . |
| WO 85/02009 | 5/1985 | WIPO . |

*Primary Examiner*—Paul Lieberman
*Assistant Examiner*—Necholus Ogden
*Attorney, Agent, or Firm*—Pillsbury Madison & Sutro LLP

[57] ABSTRACT

Compositions made up of one or more molecular alloys which are suitable for storing or restoring thermal energy at a temperature level T and over a time interval δ matching those required for a particular application as a phase-change material, said alloys belonging to a phase diagram having a transition region within a temperature range which includes the required temperature and has a near-horizontal geometric locus (EGC). Said compositions are useful as a phase-change materials, particularly in the agrifoodstuffs and paramedical industries.

22 Claims, 9 Drawing Sheets

MOLECULAR ALLOYS FOR STORING AND RESTORING THERMAL ENERGY BY PHASE CHANGE

The invention relates to compositions useful as phase-change materials for storing and restoring thermal energy by latent heat.

Thermal energy may be stored in two main forms, namely sensible heat and latent heat.

Storage of sensible heat in a material results in an increase in its temperature or in the case of restoration in a reduction of its temperature.

In contrast with storage by sensible heat, storage by latent heat is performed isothermally if the material is pure, or with some variation in temperature in the case of mixtures: the main factor being the phase change of the material.

Phase change materials (PCMs) are thus compounds capable of storing and restoring thermal energy by means of their phase transitions, most frequently solid-to-liquid transitions, but also solid to solid transitions.

When heated the material takes calories from the external medium and reaches a temperature $T_{tr}$ (transition temperature), passing from phase 1 to phase 2 by heat absorption. When the transition is completed, its temperature can rise again.

If the material is cooled, the converse transition takes place: at $T_{tr}$ the material passes from phase 2 to phase 1 and restores to the external medium the energy which it had previously stored, while remaining at the temperature $T_{tr}$. The energy involved is the variation in phase change enthalpy $\Delta H$.

Widely used PCMs are formed by ice and saline hydrates. Certain eutectics have also been proposed. However, these materials have the disadvantage of operating at a single, non-adjustable temperature. A number of them, more particularly the saline hydrates, are corrosive and melt irregularly, frequently causing segregations which are difficult to control and which make the materials behave poorly in thermal cycling.

It has also been proposed to use organic compounds such as fatty acids, paraffin waxes or certain paraffin wax mixtures for the storage of energy.

Thus, French Patent 2 368 529 discloses the use of paraffin wax mixtures which are solid at 25° C. as PCMs. However, the aim of that patent is to improve the thermal properties of such mixtures by the addition of metals, their oxides or their silicates. The example given relates to improving the thermal properties of an 82/18 mixture of n-docosane/n-tetracosane by the addition of magnesium oxides, alumina, emery, kaolin and aluminium in the proportion of 25 to 55% by weight.

However, this patent does not consider the advantage of the mixture of paraffin waxes as such, or the conditions to be combined to enable it to meet the demands of a given application at a defined temperature.

Applications W087/03290, EP 0 344 013 and EP 0 344 014 disclose polyolefine composites containing phase change materials formed more particularly by mixtures of paraffin waxes of $C_{14}$ or above. These composites are intended for the storage of solar energy.

The paper given by Salyer at the 15th North American Thermal Analysis Society Conference, Cincinnati, Ohio, Sep. 21–24, 1986, relates to the analysis of crystalline paraffinic hydrocarbons more particularly intended for the storage of solar energy. Mixtures of commercially available paraffin waxes are studied as regards their properties as phase change materials for this application.

That study relates to mixtures of alkanes in given proportions and formed by odd chains—i.e., chains with an odd number of carbon atoms (referred to hereinafter as Cni) (mixtures C15/C19, C17/C19); even chains—i.e., with an even number of carbon atoms (referred to hereinafter as Cnp) (mixtures C14/C16, C16/C18, C16/C20); even and odd chains (C16/C17, C18/C19) or by Cni or Cnp of longer chains (>C20). Ternary mixtures are also reported (C16/C17/C18; C17/C18/C19; C16/C18/C20; C17/C19/C21; C14/C17/C20 and C16/C19/C21), all used in the concentration 0.25/0.50/0.25.

Similarly, Salyer reports on the results obtained with synthesised multi-component mixtures corresponding to commercially available products.

However, the conditions used for the measurements do not allow a proper assessment of the characteristics of the mixtures studied, nor therefore to determine for what temperature they are really appropriate; neither are the means stated for obtaining compositions for a particular temperature, for example, one required precisely in a given application.

The work carried out by the Inventors in this field has shown that to make highly reliable compositions which are actually suitable, the starting compounds must meet precise demands evaluated by strict methods.

This work led to the working out of novel compositions and novel phase change materials.

It is therefore an object of the invention to provide novel compositions worked out with reference to predetermined parameters which by their phase change enable high quantities of energy to be stored and restored by latent heat.

The invention also relates to the preparation of said phase change compositions.

It also relates to the use of compositions of this kind as materials having a phase change over a narrow temperature range lying in a temperature band enabling industrial needs to be widely satisfied.

The compositions according to the invention, suitable more particularly for storing and restoring thermal energy by latent heat, are characterized in that they are formed by one or more molecular alloys, being characterized as such by X-rays, capable of storing or restoring thermal energy at a temperature T over a temperature range δ as required for a particular application as a phase-change material, belonging to a phase diagram having, if the alloy is binary, a loop in the case of total miscibility, or a partial loop in the case of partial miscibility, or, if the alloy is ternary or above, a transition zone, said loop or zone lying in a temperature band including that which is required for a given application and whose geometric locus EGC (Equal G Curve) is slightly curved and close to horizontal, to ensure a δ not exceeding the required width, having a behaviour satisfactory for thermal cycling, said alloys being obtained from organic compounds having the latent heat conventionally required to be phase-change materials, having a degree of molecular homeomorphism $\epsilon_k$ higher than 0.8 and, preferably, higher than 0.9 for the binary alloys, or having said property for the various constituents taken in pairs if they are multi-component alloys, whose inter-molecular interactions are relatively comparable for the structures of the various constituents.

The term "molecular alloy" means a single phase generated from the organic compounds used for its production, said phase behaving like a pure body from the aspect of crystallography. This single phase, obtained by syncrystallization can also be referred to by the terms: solid solution or mixed crystal.

The X-ray analyses were carried out by powder defractometry, more particularly in a Guinier Lenné or Guinier Simon chamber.

The term EGC (Equal G Curve) means the geometrical locus of the points where solid and liquid (or solid 1 and solid 2) are in equilibrium at the transition (for a binary), or in a general way the various phases in equilibrium at the transition have the same Gibbs energy (Ref: H.A.J. OONK, PHASE THEORY, ELSEVIER 1981).

The expression "satisfactory behaviour in thermal cycling" as used hereinbefore means that repeated cycles of storing/restoring, more particularly exceeding 30 cycles in the case of low-repetition applications and approximately 5000 cycles in the case of highly repetitive applications, cause neither chemical modification nor segregation which might cause the material to deteriorate.

The temperatures and associated enthalpies are measured by differential calorimetric analysis following calibration performed according to the invention in strictly the same experimental conditions as those of the analyses, which enables compositions to be provided which are completely characterized more particularly as regards their thermodynamic properties and which will be fully adapted to the envisaged application at a given temperature level.

The degree of molecular homeomorphism $\epsilon_k$ of the organic compounds used to form the alloy is obtained by so superposing the two molecules in question that the volume of overlap $\Gamma$ is a maximum, in which case their non-overlapping volume in that position, $\Delta$ is a minimum. The degree of homeomorphism is given by the formula:

$$\epsilon_k = 1 - \frac{\Delta}{\Gamma}$$

$\epsilon_k$ approaches 1 as the sizes and shapes of the molecules approach uniformity. The practical method of obtaining $\epsilon_k$ will be found in the reference Haget et al., J. Appl. Cryst (1990), 23, 492–496.

Thus, for practically all temperatures compositions are available whose thermal behaviour in melting and solidification are comparable with that of pure compounds.

The molecular alloys according to the invention, which form phase-change materials and which are also referred to hereinafter by the abbreviation PCMMAs, have a thermal efficiency window $\delta$, defined at 95% of $\Delta H$.

In this regard it will be recalled that the transition, more particularly the melting, of an alloy is a continuum extending from $T_{solidus}$ to $T_{liquidus}$. The total storage interval is equal to $|T_{sol}-T_{liq}|$. The temperature $T_{95\%}$ (lying between $T_{sol}$ and $T_{liq}$) of the PCMMAs is such that 95% of the transition energy is stored between $T_{95\%}$ and $T_{liq}$.

The range $\delta=|T_{95\%}-T_{liq}|$ is therefore an efficiency window of the PCMMA (at 95%).

The PCMMAs will hereinafter be characterized by $T_\delta$, T being taken to be equal to $T_{liq}$.

The invention relates more particularly to the compositions defined hereinbefore in which $\delta$ does not exceed approximately +8° C., more particularly +6° C., in a temperature band between −100° C. and +300° C.

Compositions particularly preferred according to the invention have a thermal efficiency window not exceeding approximately +4° C., as measured in the strict conditions set forth hereinbefore, and advantageously not exceeding +2° C., and even +1° C.

In one embodiment of the invention the organic compounds used to form the molecular alloys are not miscible in all proportions prior to the transition, but the level of invariancy which therefore characterizes the phase diagram is narrow, of the order of a few per cent in concentration, and in general shifted towards one of the starting compounds. The crystalline forms involved are not necessarily isomorphic. There are two possible cases: the shapes are non-isomorphic, in which case there are two kinds of solid alloys each characterized at a given temperature by a G curve, or the shapes of the starting constituents are isomorphic, but their degree of isomorphism is not sufficient to lead to complete miscibility; a single G curve is sufficient to describe all the alloys (at a given temperature T), but it has two points of inflection, only those alloys being stable and therefore usable whose concentrations are outside the segment of double tangence.

In either case the portion(s) of the phase diagram(s) in question is (are) the one(s) situated outside the level of invariancy.

In another embodiment of the invention the organic compounds used to form the molecular alloys are miscible in all proportions prior to the transition.

Their crystalline shapes are therefore isomorphic and their degree of crystalline isomorphism $\epsilon_m$ is close to 1.

The degree of crystalline isomorphism $\epsilon_m$ is defined for two compounds (a notion which can be generalized if necessary by taking the compounds in pairs in the case of multi-component alloys) by so superposing the crystalline lattices of the two compounds in question that the volume of overlap $\Gamma$ is a maximum; in that case their non-overlapping volume, $\Delta_m$, in that position is a minimum, and $$\epsilon_m = 1 - \Delta_m/\Gamma_m$$

(Ref. Haget et al, given hereinbefore).

The solid-liquid loop can have three appearances:

that of a simple cigar shaped domain: the alloys which can be produced from the organic compounds will have a melting range intermediate those of the constituents of the alloy, that of a loop with a minimum point; in this case an alloy can be produced which melts at temperatures lower than those of the compounds;

that of a loop with a maximum Gibbs point, certain of the alloys obtained melting at a temperature higher than that of the starting compounds.

In another embodiment the miscibility of the compounds used is low; the phase diagram is characterized by a wide level of invariancy of eutectic type; a mixture of alloys is obtained which is particularly advantageous due to its thermal window ($\delta=0$) for the eutectic concentration and which operates at the temperature of the eutectic invariant. The compounds have small $\epsilon_k$s; they are either non-isomorphic, or isomorphic with low $\epsilon_m$s.

According to another embodiment of the invention the compositions in question are also characterized in that they contain one or more of the afore-defined organic compounds by way of doping agents present in molar proportions of at least 5%, the main compound(s) being present in a proportion of approximately 90% or more. This doping advantageously enables T to be adjusted in relation to a given application.-

The molecular alloys according to the invention correspond more particularly to formula (I):

$$A_{x_a} Z_{x_z} \qquad (I)$$

wherein
- A is an acyclic or cyclic, saturated or unsaturated, optionally substituted organic compound, excluding benzene and substituted benzenes,
- Z denotes one or more organic compounds differing from A but selected from the meanings given for A,
- the organic compounds represented by A and Z meeting the afore-defined criteria, and
- $x_a$ and $x_z$ denote the molar proportions of A and Z respectively.

The term acyclic organic compound means the straight or branched chain compounds having 2 to 120 carbon atoms, and more for the polymers. These compounds are preferably alkanes, alkenes or alkynes.

The cyclic organic compounds are formed by one or more rings having 5 to 30 carbon atoms, more particularly aromatic rings, such as naphthalene, anthracene, benzene being excluded. As a variant they are formed by one or more heterocyclic compounds. The heterocyclic compounds are advantageously selected from the nitrogenated heterocyclic compounds, for example imidazoles, pyridine, pyrimidine, pyridazine, oxygenated heterocyclic compounds such as the oxazoles, oxygenated and nitrogenated heterocyclic compounds such as the oxadiazoles or else sulphurated heterocyclic compounds such as thiaizole. According to another embodiment the cyclic organic compounds contain one or more carbon rings and one or more heterocyclic compounds.

The organic compounds represented by A and Z optionally contain one or more substituents selected from the halogens F, Cl, Br, I, the —OH or —OR$_1$ groups, the alkyl, the alkene and alkyne groups, these various groups preferably having 1 to 8 carbon atoms, more particularly 1 to 4 carbon atoms, the —COOH, —COOR$_1$, —COR$_1$, —CH$_2$OH, —CH(R$_1$)—OH, —C(R$_1$, R$_2$)OH, or their ethers, —CHO,

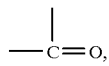

—CONH$_2$, —NH$_2$, —NH(R$_1$), or —N(R$_1$, R$_2$), =S, —SH, —NO$_2$, R$_1$ and R$_2$, which are identical or different, being an alkyl group having 1 to 8 carbon atoms, preferably 1 to 4 carbon atoms, functional groups, for example, amine, ketone, sulfhydryl, amide, possibly forming one or more moieties of the chain. The substituents of the acyclic organic compounds also contain the afore-listed rings and heterocyclic compounds.

In the acyclic organic compounds or their ethers, the above substituents occupy any position on the carbon chain, and/or are situated at one or both ends of the chain.

In the cyclic organic compounds, these substituents occupy any position on the ring.

In a family of molecular alloys according to the invention, A and Z belong to the same class of compounds.

One group of this family is formed by hydrocarbon chains, more particularly alkanes, alkenes or alkynes, except for the mixtures expressly disclosed in the prior art documents mentioned hereinbefore.

Particularly preferred molecular alloys are prepared from straight or branched chain, optionally substituted, alkanes containing from 8 to 100 carbon atoms, as indicated hereinbefore.

The molecular alloys prepared from normal alkanes, having the chemical formula $C_nH_{2n+2}$ ($C_n$ for short) will be referred to hereinafer by the term ALCAL.

In this family all the intermolecular interactions are of Van Der Walls type, giving very low $\Delta G_{excess}$ both for solid solutions and for liquid solutions, which induces only slightly curved EGC curves.

The ALCALs deemed to be acceptable—i.e., meeting the afore-defined criteria—exhibit excellent behaviour in thermal cycling; they can withstand several thousand cycles without damage (on condition that sublimation is avoided, which might alter their composition). This is due to the joint actions of the low δ, the fact that they are chemically inert, and the fact that their densities are similar. Moreover, supercooling phenomena are very slight or even non-existant, as long as conditions of utilization are maintained which are close to those of the application envisaged hereinafter.

They also have the advantage of being chemically inert, non-corrosive and water-impermeable. They are also acceptable from health considerations.

Acceptable ALCALs, covering a wide temperature band, for example, as most generally required in industry, are formed by chains having from 8 to 100, more particularly from 8 to 50 carbon atoms.

In these ALCALs, the constituent chains are Cnp or Cni or else Cnp and Cni. The chains can be consecutive, of the type Cni/Cni, or Cnp/Cnp or Cni/Cnp, or Cnp/Cni. As a variant, they differ by a number of moieties, more particularly by more than 4 or 5 carbon moieties. ALCALs may be mentioned, for example, which contain at least one chain having 14 carbon atoms or more, the or each other chain containing more than 5 supplementary carbon moieties.

In one particular arrangement according to the invention, the aforementioned ALCALs contain at least one chain having one or more substituents, for example, those defined hereinbefore.

Among these substituents the carboxyl groups, esters and halogens may be mentioned; they can advantageously occupy one or both of the ends of the chain.

In dependence on the requirements for a given application, a man skilled in the art will select the most appropriate substitutions to obtain the required value T. Similarly, the proportions of each chain will readily be selected by considering the diagrams of attributes δ, as illustrated by the Examples.

As indicated hereinbefore, one or more of the constituents of the ALCAL can be present by way of doping agent. The molar proportion of each doping agent is in that case of the order of less than 5%.

In another group, the alloys of the invention are prepared from monocyclic or polycyclic, more particularly aromatic organic compounds, with the exception, as indicated hereinbefore, of substituted or unsubstituted benzene.

In one embodiment, heterocyclic compounds are used.

In yet another group the alloys are formed from hydrocarbon chains containing one or more rings and/or one or more heterocyclic compounds.

It will be recalled that in one advantageous embodiment of the invention, the various alloys are doped.

In yet another group according to the invention, the organic compounds are polymer chains.

In another family of alloys according to the invention, A and Z belong to different classes of compounds.

Preferred alloys of these different families are binary and correspond to the formula (II):

$$A_{x_a} B_{x_b} \quad (II)$$

where $x_a + x_b = 1$, i.e., $A_{1-x} B_x$

Other alloys are ternary and have the formula (III):

$$A_{x_a} B_{x_b} C_{x_c} \quad (III)$$

where $x_a + x_b + x_c = 1$

Yet other alloys are quaternary and correspond to the formula (IV):

$$A_{x_a} B_{x_b} C_{x_c} D_{x_d} \quad (IV)$$

where $x_a + x_b + x_c + x_d = 1$

In these formulae the various constituents A, B and, where applicable, C and D and the indexes corresponding to the respective molar concentrations correspond to the requirements defined hereinbefore and B, C and D have the meanings given hereinbefore for A, but differ from one another.

Other alloys contain more than four organic compounds, namely 5, 6 or more.

The invention also relates to a process for the preparation of the compositions defined hereinbefore.

For this purpose, use is made of the organic compounds defined hereinbefore in the proportions required in the final alloy, said compounds being subjected to conventional techniques such as melting/crystallization, melting/quenching, dissolution/evaporation, simultaneous sublimation, zone levelling or chemical inter-diffusion. The zone levelling technique is described more particularly by W. J. Kolkert, thesis 1974, Utrecht, Netherlands.

In one advantageous embodiment of the invention, to prepare the ALCALs when all the Cns are liquid at ambient temperature, the required liquid solution is formed by mixing and agitating the starting compounds used in the proportions required in the alloy. When some or all of the starting Cns are solid, the base products are dissolved in appropriate proportions in a mutual solvent, for example ether, whereafter the solvent is evaporated (preferably in an inert gas flow). Alternatively, the weighed products are subjected to melting with agitation to ensure the homogeneity of the product, whereafter they are quenched.

As a variant, the compositions according to the invention are obtained by separational methods, this having the advantage of using the byproducts of the oil industry. A mixture of organic compounds containing the required composition is therefore subjected to an extraction stage in order to isolate said composition. When the mixture does not contain all the required organic compounds and/or in the required proportions, the mixture is so treated as to increase its content of one or more constituents or to eliminate one or more constituents, as the case may be, until the required composition is obtained.

In a general way, the invention provides a number of acceptable formulations for the same temperature, enabling a selection to be made in accordance with the economic conditions and/or the availability of the base products.

The use of alloys enables the content to be selected and therefore the proper formulations to be sought for an optimum yield of the stored energy and/or to meet demands as regards the temperature of utilization and/or the required thermal window δ.

The work carried out has enabled the feasibility to be demonstrated from at least three very advantageous functions, namely those of:

energy pick-up: molecular alloys enable considerable quantities of heat to be stored and restored practically at constant temperature; super-cooling is very low or even non-existant at the kg level, and even at the mg level in the particular case of the ALCALs, temperature smoothing: a space enclosed by a molecular alloy according to the invention can be maintained at approximately the temperature T (including in the transition range of the alloy). When the exterior undergoes wide thermal fluctuations, the increase in temperature is reduced by the storage of heat in the form of latent heat, and any sudden drop in temperature would itself be minimized by the converse transformation, thermal screening: the molecular alloys can be used to slow down the effect of a thermal wave.

The tests carried out (mg, g, kg levels) on the molecular alloys according to the invention have shown that these materials more particularly have excellent yields and thermal reliability and that their behaviour in thermal cycling is remarkable.

By way of example, a guarantee of 30 years of service life can be ensured for day-to-day cycling of molecular alloys whose melting range does not exceed 4° C. and the density of whose constituents is similar, which is the case with the alkanes. (All properties which the saline hydrates and conventional PCMs do not possess.)

The advantageous properties of the compositions defined hereinbefore are enjoyed by using them as phase change materials for the storage and restoration of energy at a given level of temperature, for example, that required for a particular application.

The invention relates therefore to the application as phase change material of the compositions formed by one or more molecular alloys, as defined hereinbefore, said application being characterized in that use is made of a composition suitable for storing and restoring thermal energy at a temperature T over a temperature range δ which strictly meet the requirements of a given application.

The invention relates more particularly as PCMMAs, to the various compositions $A_{xa} Z_{xz}$ defined hereinbefore in packaging appropriate for a given application.

In these applications the basic principal rests on the fact that a situation of thermal dynamic non-equilibrium will be created and will necessarily be followed by a path proceeding towards return to equilibrium. The PCMMA will either heat up, taking calories from the external medium to melt, or will cool down, restoring heat to the external medium to solidify. In both cases the transition will take the form of a long quasi-isotherm, its slope being gentler in proportion as δ is smaller.

As a result of the aforementioned characteristics, the PCMMAs according to the invention enable numerous needs to be met which have not hitherto been satisfied in very varied fields. Examples are the agricultural feedstuffs and paramedical fields, and those connected with domestic protection or utilizations.

Thus, in the agricultural feedstuffs field, all the problems of not breaking the cold chain are concerned. The alloys according to the invention can provide answers for the thermal protection and/or transport of foodstuffs typically at between approximately −50° C. and +100° C.

In the range from approximately −50° C. to −10° C., these PCMMAs are more particularly suitable for the bulk or individual transport of frozen products, or for their preservation. Their use therefore provides a bulwark against power cuts in freezers (commercial and domestic) by equipping the freezers with suitable PCMMAs.

The use according to the invention of the PCMMAs disclosed hereinbefore also has great advantage in the temperature range of approximately −10° C. to +6° C. Thus it enables beverages and ices to be reliably transported in the best conditions, for example, in ice-machine-type devices, while keeping them at the required temperature. It is also possible to produce plates, dishes or dish supports ensuring the required freshness.

The PCMMAs acceptable in this temperature range can also be used for the preparation of refrigerated displays, as required, for example, by fish merchants.

The PCMMAs according to the invention are also found to be very valuable in a temperature range between +6° C. and +16° C., which is that required for foodstuffs which are not to be frozen but require storage and/or tasting at a relatively low temperature, for example, milk products, "fourth range products" and wines requiring to be "chambré".

The PCMMAs having a phase transition temperature higher than +16° C. and more particularly up to +35° C. are advantageous for cooling certain other wines requiring a higher temperature for their consumption, and in cooking for butter, sauce and yogurt containers or containers for sour doughs or for the preservation of pastries or warmed tarts.

In higher temperature bands, between approximately +35° C. and +100° C., the PCMMAs defined hereinbefore can be used to ensure the thermal stabilization of devices, for example, fermenters, between +35° C. and +37° C., or for keeping them hot at a stable temperature up to temperatures of approximately +100° C.; for example cooked dishes (being of great advantage to caterers, more particularly in home deliveries, cafeteriors, factory restaurants, large areas), dishes, dish supports, feeding bottles, plates of porridge, hot dishes, hot plates, meal trays, hot beverages.

An edible dye and/or flavouring will advantageously be associated with the ALCAL to warn the customer if there has been an accidental leakage into the foodstuff.

PCMMAs particularly suitable for these applications are formed by molecular alloys having a thermal window not exceeding +2° C. or preferably +1° C., or even less.

In this respect the ALCALs form particularly high-performance PCMMAs which, moreover, are acceptable from the health aspect.

Different formulations of ALCALs having a transition temperature T in the aforementioned ranges are given in the Examples. Of course, other suitable formulations will readily be worked out with reference to the various parameters defined hereinbefore.

Staying with consecutive Cns (the same parity or not), the temperature level plays a relatively decisive role as regards both the possibilities of crystallization and the δ attribute, all the more so since it goes hand in hand with the $\epsilon_n$ level.

This coefficient is used to assess the degree of molecular homeomorphism $\epsilon_k$. $\epsilon_n$ is defined as follows $$\epsilon_k = 1 - \frac{\left\lceil \frac{\Sigma Code}{0001} \right\rceil n}{n_{minimum}}$$

where $\Delta n$ is the difference $n_A - n_B$ between the two molecules $Cn_A$ and $Cn_B$ to be compared, and $n_{minimum}$ is the value of n of the shortest molecule.

At low temperature, advantageous embodiments are mainly derived from eutectic mixtures of ALCAL (with δ=0° C.); as the temperature T rises, the limits of syncrystallization will increase and the high-attribute ranges will become larger.

If non-consecutive Cns are selected, the roles of the ΔTs and the $\epsilon_n$s will act in the same direction and be added to the T effect explained hereinbefore. Thus, a considerable difference between the nAs and nZs will be associated with ΔTs which are higher and $\epsilon_n$s which are lower in proportion as T is lower. Conversely, the higher the value of T the more ALCALs having acceptable δs will be available with distant ns, with the consequent extended possibility of having different formulations for a required Tδ, since in that case the number of constituents can be more readily increased.

Amongst the ALCALs, those will be mentioned which are formed more particularly by chains having C8 to C16, more particularly each of these doped alkanes, the consecutive or non-consecutive, possibly also doped binaries, ternaries, quaternaries or higher, with molar proportions such that the $T_\delta$ values correspond strictly to the requirements.

The applications mentioned hereinbefore will advantageously be put into effect with ALCALs the majority of which contain chains having more than 14 carbon atoms, possibly doped.

In the paramedical field the applications are also highly various and more particularly cover a temperature range of between −80° C. and +75° C.

Sectors particularly involved comprise packaging, the protection of instruments, isothermal or control-temperature manipulations, the design of isothermal clothing, functional difficiencies and treatments of symptoms.

For applications relating to packaging and/or transport, with non-breakage of the cold chain, advantageously PCMMAs are used which are acceptable at a given temperature, in a range of from approximately −80° C. to +16° C.

Thus, PCMMAs having a phase change at a temperature close to −80° C. are particularly useful for the preservation and/or transport of bone grafts and/or tendons, plasma or serum.

PCMMAs acceptable at about −30° C. enable medicines or plasma to be transported in peak condition.

It is particularly advantageous to use PCMMAs acceptable around −20° C. for bone banks or for postmortem transport.

At higher temperatures, the PCMMAs ranging from approximately −10° C. to +6° C. offer great advantages. They are therefore advantageously used more particularly for transporting organs or amputated limbs and for the preservation of red globules or organs.

PCMMAs having phase transitions in a range of between +6° C. and +16° C. are also very advantageous. They more particularly enable various kind of tissues or cells, such as corneal grafts or certain sperms to be preserved. They also allow the preservation of vaccines which can thus be transported and are available for patients at the site of an accident.

In a temperature range above approximately +16° C., the PCMMAs are more particularly used for the transport of medicines.

Other applications in the paramedical field relate to isothermal or control-temperature manipulations.

The PCMMAs according to the invention which have a transition temperature in a range of approximately −80° C. to −10C are more particularly suitable for cryomicrotomy, for example, for rachis or joints. Those which have a transition temperature in a range of approximately −10° C. to +6° C. are very useful for the thawing of plasma and cells, for haemodynamic investigation, the analysis of blood gases, sterile tissue samplings, for example, of muscles or vessels, and cell cultures.

The PCMMAs having high transition temperatures, more particularly in a temperature range of +20° C. and above can be used, in increasing order of temperature, for culture boxes and sample carriers (from +20° C. to +50° C.), in nerve electrophysiology (between +30° C. and +35° C.), for the heating of transplants, for enzymatic tests (between +35° C. and +37° C.) and for the heating of blood prior to transfusion (towards +37° C.).

Other applications in the para-medical field relate to functional difficiencies and treatments of symptoms.

The PCMMAs according to the invention having a phase transition

- in a range of approximately −10° C. to +6° C. are more particularly suitable for pre- and post-operational care, more particularly in ophthalmology (between 0° C. and +6° C.)
- in a range of approximately +6° C. to +16° C., for veterinary treatment and in cryotherapy, for example, to produce dressings for sprains and,
- in a temperature range above +16° C. in cryotherapy, to obtain refreshing effects and more particularly for certain forms of care (around +35° C.);
- for the range above +37° C. they would be useful for incubators or for the local or general heating of patients during operations or in post-operative care (coverings, mattresses, for example, mattresses incorporating reinforcement in which the PCMMAs can be associated with other materials, such as fibrous or expanded materials, for reasons of comfort). Autonomy of operation will be prolonged by thermally insulating layers on the external surfaces not in contact with the patient.

They will also be useful in heat treatments for example for rheumatism, or for producing latent heat packs.

To facilitate use in the family circle, more particularly in this kind of application, added to the PCMMA is a small amount of colouring agent of edible quality, so as not to disturb the health acceptability of the materials. This feature enables the T of the application to be readily defined (examples: blue for T=+6° C., green for +25° C., colourless for +35° C., yellow for +39° C., orange for +45° C. and red for +50° C.). The doctors will of course provide prescribe the use of any particular temperature range.

Lastly, it will be noted that the availability of PCMMAs with a $T_S$ attribute at the required T offers practitioners the possibility of carrying out clinical tests at different temperatures in order to discover the most suitable ones.

In these applications in the paramedical field with the different temperature levels in question, it is more particularly advantageous to use PCMMAs formed by ALCALs, possibly containing functional groups.

The PCMMAs according to the invention also enable the problems to be solved which are connected with the safety and/or protection of products, installation and premises. These applications relate to a wide temperature range typically extending from −80° C. to +200° C.

They provide a very advantageous solution more particularly for

- the transport of flammable and/or dangerous chemical products at low temperature,
- the protection of electrical installations and electronic or information systems, in which they are possibly coupled with alarm systems (the temperature ranges for this kind of use are very varied and may extend up to +200° C. and more, for example, in the case of fires), a particularly advantageous temperature range being between +70° C. and +90° C.,
- protection against sudden power cuts, avoiding the necessity of very costly contracts concerning non-interruptable power supply in installations requiring iso-thermal maintenance, for example, fruit or vegetable ripening units or fermentation vats.

The PCMMAs according to the invention are also particularly useful in the field of protection as a solution to energy saving problems. They form highly efficient protection means, for example, "cumulus", hot baths, giving extra comfort, thermal reservoirs for heat pumps (notches from +45° C. to +55° C. for hot sources and from +3° C. to +10° C. for cool sources), cold thermal screens for large assemblies (range from +4° C. to +8° C.), or for domestic heating (by latent heat), being integrable as a decorative element (transparent or opaque objects, for example, statues).

They can also be used in cultures, more particularly ensuring the production of plant roots in glasshouses, avoiding the complete heating of the glasshouse, or in sample carriers.

In domestic or industrial applications, the PCMMAs according to the invention will be advantageously used for articles independently used in the home or outside, such as hair curlers, irons, feeding bottles, for example when camping.

They also enable increasing or decreasing thermal gradients to be readily produced which can be as strong or weak as required and can therefore be used for regulating enclosures in which there is a thermal gradient such as those, for example, required in growing crystals.

In the various applications mentioned hereinbefore, for the production of the PCMMAs use is advantageously made of substituted or unsubstituted, possibly doped ALCALS, and also of the cyclic and heterocyclic compounds as defined hereinbefore. Other advantageous molecular alloys contain hydrocarbon chains which differ from the alkanes with functional groups. Yet other molecular alloys are formed by polymer chains.

Clearly, in the various applications of the PCMMAS, the method of use can be diversified; a PCMMA can be used on its own (or) associated with one or more other PCMMAs and/or PCMs so as to form multiple layers (which can advantageously be used to form temperature gradients).

In numerous applications the PCMMA operates in conjunction with an energy source.

In general, the invention supplies the means for producing the most suitable materials for a given application. Such production is all the more facilitated by the fact that the compositions according to the invention are malleable. The liquid compositions are thus perfectly suited and are solidified in an appropriate shape.

The PCMMAs are packaged in structures adapted to their use.

In general, the packaging comprise a double wall of a material having a high heat insulation capacity, at the very least the wall in contact with the external medium when the two walls are produced using different materials.

Suitable materials include glass, metals, the material commercially available under the trade mark PLASTISHIELD$^R$, based on glass and polymers, and also plastics materials and expanded polymers with closed cells.

The following may be mentioned by way of example: the polyolefines, such as high density (HDPE) or low density (LDPE) polyethylene or polypropylene (PP), the polyesters, more particularly ethylene polyterephthalate or acrylates, the styrenes, such as polystyrene (PSE) or expanded polystyrene (ES), or acrylonitrile-butadiene-styrene (ABS), the polyamides (PA), the polyvinyls, such as polyvinyl chloride (PVC), the fluorinated polymers, such as polytetrafluoroethylene (PTFE).

These materials allow smooth, undulating or alveolated surfaces to be produced.

If necessary they can be reinforced, for example, with struts, to ensure that the structure behaves satisfactorily.

For their shaping, the usual plastics converter and processor techniques are used; thus, injection, injection/ blowing, injection/blowing by biorientation, extrusion/blowing, blowing or rotational moulding methods are used to product flasks, drums, bottles, flagons, pitchers, kegs, casks, vats, reservoirs, jars, boxes.

Thermoforming or injection are used to produce alveolated or non-alveolated, reinforced or non-reinforced pots, goblets, troughs, bell jars, meal trays and also clipping devices.

Advantageously extrusion or calendering techniques are used when the packaging does not require a double wall, for example, to produce receptacles such as pouches, flexible doses, cartridges, sheaths, bags, sachets, briquettes.

The packaging is filled with the PCMMA using the liquid or pulverulent composition.

If necessary liquid alloy can be preshaped, placed in a matrix and solidified using liquid nitrogen. In that case it can be transferred in the solid state to the final packaging.

The invention will be illustrated hereinafter by examples of the preparation of molecular alloys and their applications as PCMMAs.

Figure 9:
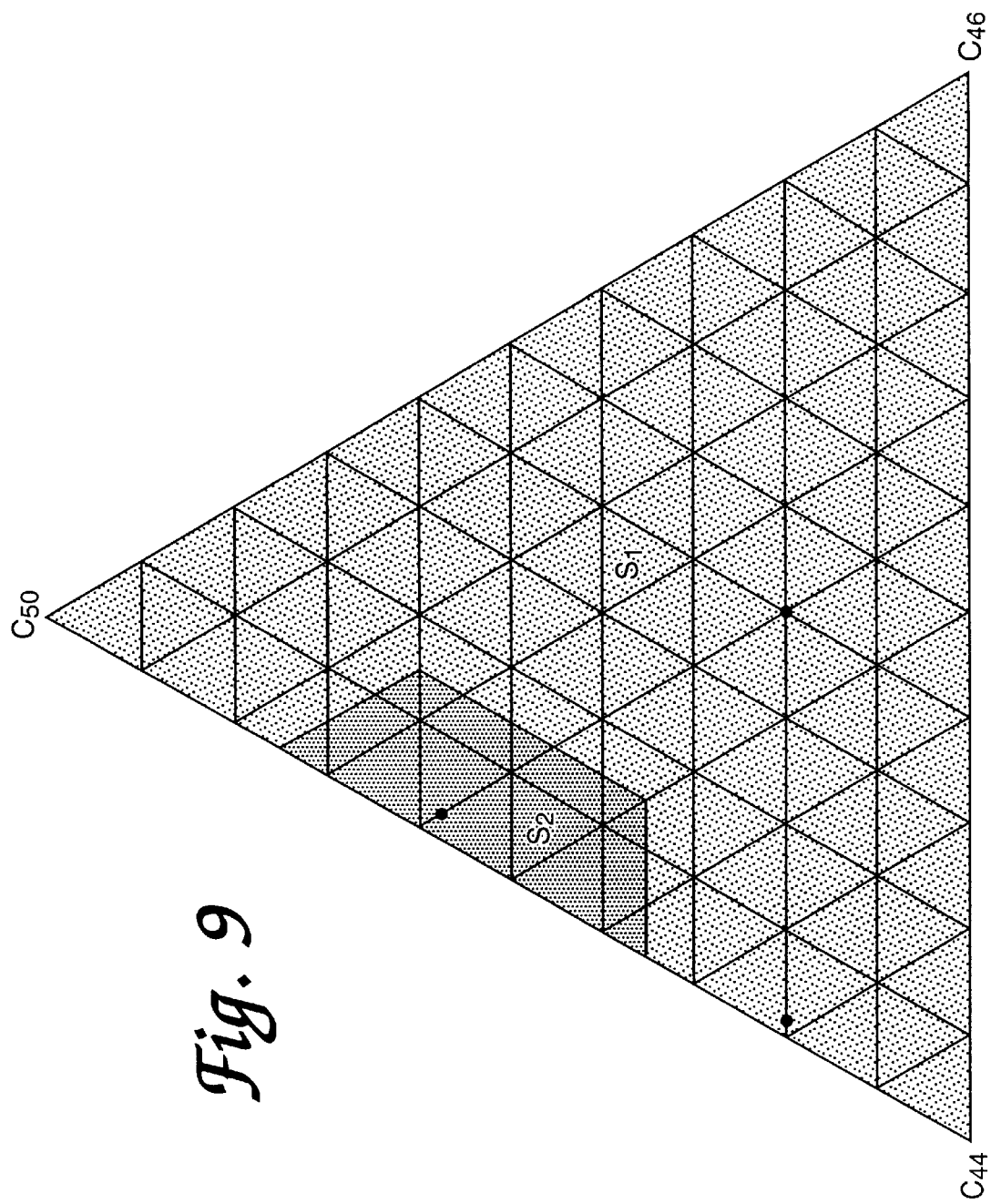

In the examples reference is made to FIGS. 1 and 9, which are diagrams giving the attributes δ of various ternary molecular alloys.

Characterization of the materials

1. X-ray analysis (Guinier-Lenné, Guinier-Simon) to define the number and nature of the phases present in relation to temperature, demonstrate the phase changes and prove that prior to melting the materials actually take the form of alloys (and not mixtures of starting compounds).

2. Differential calorimetric analysis (AED, DSC) for the precise determination of the pertinent temperatures and the associated enthalpies, observing the two following criteria:
   preliminary calibration carried out strictly in the same experimental conditions as these of the analyses.
   use of the AED or DSC signals by the "shape factors method" developed by Haget et al, Calorim. Anal. Therm. (1987), 18, 255, and Courchinoux et al., J. Chim. Phys. (1989), 86, 3, 561.

The following Examples 1 to 5 relate to the ALCALS, Examples 6 to 9 to molecular alloys containing or formed by chains having an acid function, and Examples 10 to 12 to applications of the molecular alloys according to the invention. (It will be noted that in the values of $T_\delta$ and δ given in the examples, T and δ are in °C.).

Examples 1 to 7 concern respectively

Example 1 the formulation of doped ALCALs,

Example 2 the formulation of doped binary ALCALs,

Example 3 the formulation of doped ternary ALCALs and higher.

Example 4 study of the evolution of binary ALCALs, binary ALCALS of the same parity [1) consecutive; 2) non-consecutive], binary ALCALs with different parity [1) consecutive; 2) non-consecutive], Example 5 ternary ALCALs:
   a) study of the evolution of ALCALs [1) consecutive; 2) not directly consecutive],
   b) various formulations of ternary ALCALs (1 to 9).

Remarks concerning the alcanes

When $8 \leq n \leq 20$, prior to melting the alcanes having odd ns (Cni) are of hexagonal form, those having even ns (Cnp) being triclinic.

When $21 \leq n \leq 43$, all the alcanes are hexagonal prior to melting.

Lastly, when $n \geq 44$, all the alcanes are orthorhombic prior to melting.

General method of preparation

When some or all the alcanes which are used are solid, first the starting alcanes are dissolved in suitable proportions in a common solvent, for example, ether, whereafter the solvent is evaporated, preferably in a flow of an inert gas, for example nitrogen. Alternatively, the products are melted and agitated, to produce a homogeneous mixture, whereafter they are soaked.

EXAMPLE 1

Formulations of doped alcanes

Table 1, which follows, presents formulations of doped alcanes. For each alloy formulation the transition temperature T is indicated in °C., the thermal window δ in °C. and the enthalpy variation ΔH in J/g.

TABLE 1

| Cn | Formulations | | | T (° C.) | δ (° C.) | ΔH (J/g) |
|---|---|---|---|---|---|---|
| C8 | $C8_{0.980}$ | $C10_{0.020}$ | | −57.2 | 1.4 | 170 |
| C9 | $C9_{0.995}$ | $C10_{0.005}$ | | −53.0 | 1.3 | 117 |
| C10 | $C10_{0.990}$ | $C11_{0.010}$ | | −29.0 | 1.2 | 196 |
| C11 | $C11_{0.998}$ | $C12_{0.001}$ | $C13_{0.001}$ | −25.0 | 1.3 | 141 |
| C12 | $C12_{0.993}$ | $C11_{0.004}$ | $C13_{0.004}$ | −9.4 | 1.2 | 210 |
| C13 | $C13_{0.998}$ | $C11_{0.001}$ | $C12_{0.001}$ | −4.7 | 0.6 | 162 |
| C14 | $C14_{0.999}$ | $C13_{0.001}$ | | +5.9 | 1.5 | 216 |
| C15 | $C15_{0.994}$ | $C14_{0.001}$ | $C16_{0.005}$ | +10.0 | 0.6 | 159 |
| C16 | $C16_{0.996}$ | $C15_{0.003}$ | $C17_{0.001}$ | +17.9 | 1.0 | 227 |
| C17 | $C17_{0.998}$ | $C15_{0.001}$ | $C16_{0.001}$ | +22.2 | 0.5 | 168 |
| C18 | $C18_{0.994}$ | $C19_{0.006}$ | | +28.4 | 0.9 | 232 |
| C19 | $C19_{0.980}$ | $C20_{0.020}$ | | +32.3 | 0.9 | 168 |
| C20 | $C20_{0.980}$ | $C19_{0.020}$ | | +36.4 | 5.0 | 240 |
| C20 | $C20_{0.994}$ | $C19_{0.006}$ | | +36.5 | 1.6 | 241 |
| C21 | $C21_{0.997}$ | $C23_{0.003}$ | | +39.9 | 0.3 | 156 |
| C22 | $C22_{0.980}$ | $C21_{0.020}$ | | +43.3 | 0.9 | 152 |
| C22 | $C22_{0.997}$ | $C21_{0.003}$ | | +43.8 | 0.9 | 152 |
| C23 | $C23_{0.996}$ | $C22_{0.002}$ | $C24_{0.002}$ | +47.5 | 0.2 | 158 |
| C23 | $C23_{0.980}$ | $C24_{0.020}$ | | +48.2 | 0.8 | 160 |
| C24 | $C24_{0.950}$ | $C22_{0.050}$ | | +50.1 | 0.2 | 157 |
| C24 | $C24_{0.930}$ | $C20_{0.050}$ | $C22_{0.020}$ | +50.5 | 1.1 | 158 |
| C24 | $C24_{0.950}$ | $C26_{0.050}$ | | +50.9 | 0.2 | 158 |
| C25 | $C25_{0.992}$ | $C24_{0.005}$ | $C26_{0.003}$ | +53.8 | 0.2 | 161 |
| C26 | $C26_{0.998}$ | $C24_{0.002}$ | | +56.9 | 0.1 | 161 |
| C26 | $C26_{0.999}$ | $C25_{0.001}$ | | +56.9 | 0.1 | 161 |

An examination of this Table shows that the different doped formulations studied have a transition over a narrow temperature range which is always less than 2° C., and does not even exceed 1° C. for the majority, the ΔHs being mainly higher than 150 J/g and even greater than 200 J/g in certain cases.

EXAMPLE 2

Formulations of doped binary ALCALs

Table 2 shows the characteristics of doped binary alloys.

TABLE 2

Examples:

| Cn–Cn | Formulation | T (° C.) | δ (° C.) | ΔH (J/g) |
|---|---|---|---|---|
| C8–C10 | $C8_{0.930}$ $C10_{0.060}$ $C9_{0.010}$ | −57.7 | 2.8 | 170 |
| C10–C11 | $C10_{0.690}$ $C11_{0.300}$ $C12_{0.010}$ | −35.9 | 2.1 | 137 |
| C10–C11 | $C10_{0.490}$ $C11_{0.490}$ $C12_{0.020}$ | −33.2 | 4.2 | 129 |
| C10–C11 | $C10_{0.310}$ $C11_{0.680}$ $C12_{0.010}$ | −30.4 | 4.2 | 125 |
| C11–C12 | $C11_{0.880}$ $C12_{0.100}$ $C13_{0.020}$ | −24.9 | 1.1 | 141 |
| C11–C12 | $C11_{0.490}$ $C12_{0.490}$ $C13_{0.020}$ | −21.6 | 2.0 | 134 |
| C12–C13 | $C12_{0.690}$ $C13_{0.300}$ $C11_{0.010}$ | −13.5 | 2.7 | 146 |
| C12–C13 | $C12_{0.480}$ $C13_{0.480}$ $C11_{0.040}$ | −11.8 | 2.2 | 146 |
| C12–C13 | $C12_{0.200}$ $C13_{0.780}$ $C11_{0.020}$ | −8.0 | 2.4 | 150 |
| C13–C15 | $C13_{0.780}$ $C15_{0.200}$ $C14_{0.020}$ | −5.0 | 1.0 | 144 |
| C13–C14 | $C13_{0.690}$ $C14_{0.300}$ $C15_{0.010}$ | −3.9 | 1.4 | 152 |
| C13–C14 | $C13_{0.485}$ $C14_{0.490}$ $C15_{0.025}$ | −2.5 | 1.8 | 152 |
| C13–C15 | $C13_{0.530}$ $C15_{0.450}$ $C14_{0.020}$ | 0 | 7.0 | 148 |
| C14–C16 | $C14_{0.790}$ $C16_{0.200}$ $C15_{0.010}$ | +2.9 | 2.0 | 159 |
| C14–C16 | $C14_{0.890}$ $C16_{0.100}$ $C15_{0.010}$ | +3.2 | 1.9 | 164 |
| C14–C15 | $C14_{0.400}$ $C15_{0.570}$ $C13_{0.030}$ | +5.2 | 3.9 | 147 |
| C13–C15 | $C13_{0.200}$ $C15_{0.790}$ $C14_{0.010}$ | +6.0 | 8.0 | 159 |
| C14–C15 | $C14_{0.260}$ $C15_{0.700}$ $C16_{0.040}$ | +7.7 | 2.0 | 155 |
| C14–C16 | $C14_{0.410}$ $C16_{0.580}$ $C15_{0.010}$ | +8.8 | 4.9 | 148 |
| C15–C16 | $C15_{0.840}$ $C16_{0.130}$ $C14_{0.030}$ | +9.5 | 1.0 | 153 |
| C15–C16 | $C15_{0.840}$ $C16_{0.150}$ $C14_{0.010}$ | +10.5 | 0.8 | 150 |
| C15–C16 | $C15_{0.640}$ $C16_{0.330}$ $C14_{0.030}$ | +10.7 | 2.0 | 152 |
| C15–C16 | $C15_{0.690}$ $C16_{0.300}$ $C14_{0.010}$ | +11.2 | 1.3 | 156 |
| C15–C17 | $C15_{0.685}$ $C17_{0.300}$ $C16_{0.015}$ | +11.3 | 1.3 | 146 |
| C15–C16 | $C15_{0.490}$ $C16_{0.500}$ $C14_{0.010}$ | +12.3 | 1.7 | 157 |
| C15–C17 | $C15_{0.480}$ $C17_{0.500}$ $C16_{0.020}$ | +14.0 | 3.0 | 150 |
| C14–C16 | $C14_{0.100}$ $C16_{0.890}$ $C15_{0.010}$ | +16.0 | 3.2 | 175 |
| C15–C17 | $C15_{0.300}$ $C17_{0.690}$ $C16_{0.010}$ | +17.0 | 4.4 | 154 |
| C16–C18 | $C16_{0.690}$ $C18_{0.290}$ $C17_{0.020}$ | +18.0 | 1.9 | 170 |
| C16–C18 | $C16_{0.550}$ $C18_{0.440}$ $C17_{0.010}$ | +19.8 | 2.0 | 165 |
| C16–C17 | $C16_{0.300}$ $C17_{0.685}$ $C15_{0.010}$ $C18_{0.005}$ | +19.8 | 1.5 | 160 |
| C15–C17 | $C15_{0.100}$ $C17_{0.890}$ $C16_{0.010}$ | +20.4 | 2.9 | 158 |
| C16–C17 | $C16_{0.100}$ $C17_{0.885}$ $C15_{0.005}$ $C18_{0.010}$ | +21.3 | 1.1 | 165 |
| C17–C18 | $C17_{0.300}$ $C18_{0.690}$ $C19_{0.010}$ | +25.7 | 1.2 | 159 |
| C18–C22 | $C18_{0.870}$ $C22_{0.100}$ $C20_{0.030}$ | +27.8 | 1.8 | 164 |
| C18–C19 | $C18_{0.800}$ $C19_{0.170}$ $C17_{0.030}$ | +27.9 | 1.5 | 156 |
| C18–C20 | $C18_{0.780}$ $C20_{0.200}$ $C19_{0.020}$ | +28.3 | 1.8 | 155 |
| C18–C19 | $C18_{0.780}$ $C19_{0.200}$ $C20_{0.020}$ | +28.4 | 1.5 | 155 |
| C18–C20 | $C18_{0.780}$ $C20_{0.200}$ $C22_{0.020}$ | +28.5 | 2.0 | 154 |
| C18–C19 | $C18_{0.580}$ $C19_{0.400}$ $C17_{0.020}$ | +28.8 | 1.6 | 156 |
| C18–C19 | $C18_{0.580}$ $C19_{0.390}$ $C20_{0.030}$ | +29.4 | 1.6 | 156 |
| C18–C22 | $C18_{0.700}$ $C22_{0.280}$ $C20_{0.020}$ | +30.8 | 3.9 | 139 |
| C18–C20 | $C18_{0.540}$ $C20_{0.450}$ $C19_{0.010}$ | +30.8 | 1.9 | 146 |
| C18–C20 | $C18_{0.530}$ $C20_{0.440}$ $C22_{0.030}$ | +30.9 | 2.0 | 146 |
| C18–C20 | $C18_{0.190}$ $C20_{0.800}$ $C22_{0.010}$ | +33.9 | 2.0 | 150 |
| C18–C20 | $C18_{0.200}$ $C20_{0.790}$ $C19_{0.010}$ | +33.9 | 2.0 | 150 |
| C19–C20 | $C19_{0.300}$ $C20_{0.680}$ $C21_{0.020}$ | +35.2 | 0.9 | 151 |
| C19–C21 | $C19_{0.290}$ $C21_{0.690}$ $C20_{0.020}$ | +35.5 | 1.2 | 151 |
| C20–C22 | $C20_{0.770}$ $C22_{0.200}$ $C18_{0.030}$ | +37.5 | 0.9 | 146 |
| C20–C22 | $C20_{0.794}$ $C22_{0.200}$ $C19_{0.004}$ $C21_{0.002}$ | +37.6 | 0.8 | 146 |
| C20–C22 | $C20_{0.800}$ $C22_{0.170}$ $C21_{0.030}$ | +37.8 | 0.8 | 146 |
| C20–C22 | $C20_{0.780}$ $C22_{0.200}$ $C24_{0.020}$ | +38.0 | 0.8 | 145 |
| C20–C24 | $C20_{0.870}$ $C24_{0.110}$ $C22_{0.020}$ | +38.6 | 1.2 | 145 |
| C20–C22 | $C20_{0.480}$ $C22_{0.490}$ $C21_{0.030}$ | +39.7 | 1.5 | 148 |
| C20–C22 | $C20_{0.471}$ $C22_{0.524}$ $C19_{0.003}$ $C21_{0.002}$ | +39.8 | 1.3 | 148 |
| C20–C22 | $C20_{0.500}$ $C22_{0.480}$ $C24_{0.020}$ | +40.0 | 1.5 | 147 |
| C20–C22 | $C20_{0.400}$ $C22_{0.580}$ $C18_{0.020}$ | +40.1 | 1.5 | 147 |
| C20–C22 | $C20_{0.376}$ $C22_{0.620}$ $C19_{0.002}$ $C21_{0.002}$ | +40.3 | 1.2 | 147 |
| C20–C22 | $C20_{0.380}$ $C22_{0.600}$ $C24_{0.020}$ | +40.6 | 1.4 | 147 |
| C20–C22 | $C20_{0.300}$ $C22_{0.690}$ $C21_{0.010}$ | +41.2 | 1.4 | 147 |
| C20–C22 | $C20_{0.279}$ $C22_{0.717}$ $C19_{0.002}$ $C21_{0.002}$ | +41.3 | 1.2 | 147 |
| C20–C22 | $C20_{0.180}$ $C22_{0.800}$ $C18_{0.020}$ | +41.8 | 1.1 | 147 |
| C21–C22 | $C21_{0.490}$ $C22_{0.490}$ $C23_{0.020}$ | +41.8 | 0.6 | 150 |
| C20–C22 | $C20_{0.184}$ $C22_{0.812}$ $C19_{0.001}$ $C21_{0.003}$ | +42.0 | 0.9 | 147 |
| C20–C22 | $C20_{0.090}$ $C22_{0.900}$ $C21_{0.010}$ | +42.8 | 0.9 | 150 |
| C20–C22 | $C20_{0.093}$ $C22_{0.903}$ $C19_{0.001}$ $C21_{0.003}$ | +42.9 | 1.0 | 150 |
| C21–C23 | $C21_{0.580}$ $C23_{0.400}$ $C22_{0.020}$ | +43.3 | 1.3 | 152 |
| C22–C24 | $C22_{0.700}$ $C24_{0.280}$ $C20_{0.020}$ | +45.2 | 0.8 | 153 |
| C22–C23 | $C22_{0.490}$ $C23_{0.500}$ $C24_{0.010}$ | +45.7 | 0.5 | 155 |
| C22–C24 | $C22_{0.700}$ $C24_{0.280}$ $C23_{0.020}$ | +45.7 | 0.9 | 152 |
| C22–C24 | $C22_{0.680}$ $C24_{0.300}$ $C26_{0.020}$ | +45.7 | 0.8 | 153 |
| C22–C24 | $C22_{0.300}$ $C24_{0.680}$ $C20_{0.020}$ | +48.1 | 0.9 | 155 |
| C22–C24 | $C22_{0.280}$ $C24_{0.700}$ $C23_{0.020}$ | +48.4 | 0.9 | 156 |
| C22–C24 | $C22_{0.300}$ $C24_{0.680}$ $C26_{0.020}$ | +48.6 | 0.9 | 155 |

TABLE 2-continued

Examples:

| Cn–Cn | Formulation | | | | T (° C.) | δ (° C.) | ΔH (J/g) |
|---|---|---|---|---|---|---|---|
| C23–C24 | $C23_{0.470}$ | $C24_{0.500}$ | $C22_{0.030}$ | | +48.9 | 0.5 | 158 |
| C22–C24 | $C22_{0.050}$ | $C24_{0.930}$ | $C23_{0.020}$ | | +50.2 | 0.4 | 158 |
| C22–C26 | $C22_{0.500}$ | $C26_{0.490}$ | $C24_{0.010}$ | | +50.2 | 2.6 | 157 |
| C24–C26 | $C24_{0.900}$ | $C26_{0.080}$ | $C20_{0.020}$ | | +50.2 | 0.4 | 158 |
| C24–C25 | $C24_{0.500}$ | $C25_{0.490}$ | $C26_{0.010}$ | | +51.7 | 0.4 | 159 |
| C24–C26 | $C24_{0.490}$ | $C26_{0.500}$ | $C20_{0.010}$ | | +52.2 | 0.9 | 158 |
| C23–C25 | $C23_{0.100}$ | $C25_{0.890}$ | $C24_{0.010}$ | | +53.0 | 0.9 | 161 |
| C24–C26 | $C24_{0.490}$ | $C26_{0.500}$ | $C22_{0.010}$ | | +53.5 | 0.9 | 162 |
| C26–C32 | $C26_{0.800}$ | $C32_{0.190}$ | $C30_{0.010}$ | | +57.3 | 2.0 | 160 |
| C28–C32 | $C28_{0.790}$ | $C32_{0.200}$ | $C30_{0.010}$ | | +62.4 | 0.4 | 160 |
| C30–C32 | $C30_{0.100}$ | $C32_{0.880}$ | $C31_{0.010}$ | $C33_{0.010}$ | +66.2 | 0.5 | 159 |
| C35–C36 | $C35_{0.890}$ | $C36_{0.090}$ | $C37_{0.020}$ | | +75.2 | 0.4 | 160 |
| C44–C50 | $C44_{0.765}$ | $C50_{0.210}$ | $C46_{0.010}$ | $C48_{0.015}$ | +86.7 | 0.7 | 223 |
| C44–C50 | $C44_{0.490}$ | $C50_{0.485}$ | $C46_{0.005}$ | $C48_{0.020}$ | +87.4 | 0.5 | 220 |
| C44–C50 | $C44_{0.395}$ | $C50_{0.585}$ | $C46_{0.005}$ | $C48_{0.015}$ | +89.2 | 1.5 | 225 |
| C46–C50 | $C46_{0.100}$ | $C50_{0.890}$ | $C44_{0.010}$ | | +91.9 | 0.6 | 215 |

EXAMPLE 3

Formulations of doped ternary and higher ALCALs

Table 3 shows the characteristics of doped ternary or higher alloys.

TABLE 3

| Alcanes | Formulation | | | | | T (° C.) | δ | ΔH (J/g) |
|---|---|---|---|---|---|---|---|---|
| C12–C13–C14 | $C12_{0.130}$ | $C13_{0.607}$ | $C14_{0.262}$ | $C11_{0.001}$ | | −6.2 | 4.8 | 130 |
| C15–C16–C17 | $C15_{0.660}$ | $C16_{0.240}$ | $C17_{0.070}$ | $C18_{0.030}$ | | +11.3 | 2.0 | 152 |
| C14–C15–C16 | $C14_{0.214}$ | $C15_{0.226}$ | $C16_{0.558}$ | $C13_{0.001}$ | $C17_{0.001}$ | +8.5 | 2.3 | 152 |
| C14–C15–C16 | $C14_{0.350}$ | $C15_{0.430}$ | $C16_{0.160}$ | $C17_{0.040}$ | $C18_{0.020}$ | +7.1 | 2.7 | 146 |
| C14–C15–C16 | $C14_{0.320}$ | $C15_{0.380}$ | $C16_{0.250}$ | $C17_{0.040}$ | $C18_{0.010}$ | +7.5 | 2.5 | 144 |
| C14–C15–C16 | $C14_{0.280}$ | $C15_{0.350}$ | $C16_{0.320}$ | $C17_{0.040}$ | $C18_{0.010}$ | +8.3 | 3.0 | 143 |
| C14–C15–C16–C18 | $C14_{0.310}$ | $C15_{0.370}$ | $C16_{0.140}$ | $C17_{0.040}$ | $C18_{0.140}$ | +7.5 | 3.4 | 127 |
| C14–C15–C16–C17 | $C14_{0.290}$ | $C15_{0.350}$ | $C16_{0.130}$ | $C17_{0.130}$ | $C18_{0.010}$ | +8.6 | 4.1 | 146 |
| C15–C16–C17 | $C15_{0.366}$ | $C16_{0.462}$ | $C17_{0.167}$ | $C18_{0.005}$ | | +13.5 | 2.0 | 154 |
| C15–C16–C17 | $C15_{0.272}$ | $C16_{0.069}$ | $C17_{0.649}$ | $C18_{0.010}$ | | +17.3 | 3.9 | 150 |
| C15–C16–C17 | $C15_{0.065}$ | $C16_{0.067}$ | $C17_{0.848}$ | $C18_{0.020}$ | | +20.6 | 2.8 | 160 |
| C18–C20–C22 | $C18_{0.850}$ | $C20_{0.065}$ | $C22_{0.065}$ | $C16_{0.020}$ | | +27.5 | 2.0 | 150 |
| C18–C20–C22 | $C18_{0.625}$ | $C20_{0.230}$ | $C22_{0.130}$ | $C24_{0.015}$ | | +30.0 | 1.9 | 142 |
| C18–C20–C22 | $C18_{0.330}$ | $C20_{0.310}$ | $C22_{0.330}$ | $C24_{0.030}$ | | +36.0 | 3.7 | 139 |
| C20–C22–C26 | $C20_{0.620}$ | $C22_{0.230}$ | $C26_{0.130}$ | $C24_{0.020}$ | | +39.5 | 1.8 | 143 |
| C20–C22–C24 | $C20_{0.340}$ | $C22_{0.320}$ | $C24_{0.310}$ | $C23_{0.030}$ | | +43.4 | 2.8 | 147 |
| C22–C24–C26 | $C22_{0.450}$ | $C24_{0.360}$ | $C26_{0.160}$ | $C25_{0.020}$ | $C27_{0.010}$ | +47.7 | 1.1 | 154 |
| C22–C24–C26 | $C22_{0.170}$ | $C24_{0.640}$ | $C26_{0.160}$ | $C25_{0.030}$ | | +50.3 | 0.8 | 156 |
| C44–C46–C48–C50 | $C44_{0.350}$ | $C46_{0.350}$ | $C48_{0.080}$ | $C50_{0.200}$ | $C47_{0.020}$ | +86.9 | 0.6 | 220 |
| C44–C46–C50 | $C44_{0.390}$ | $C46_{0.390}$ | $C50_{0.190}$ | $C48_{0.030}$ | | +87.2 | 0.5 | 224 |

EXAMPLE 4

Binary ALCALs

Study of evolution.

In this and the following Examples, the degree of molecular homeomorphism $\epsilon_k$ is determined by the coefficient $\epsilon_n$ defined hereinbefore:

where Δn is the difference $n_A-n_B$ between the two molecules $Cn_A$ and $Cn_B$ to be compared, and $n_{minimum}$ is the value of n of the shortest molecule.

I Binary ALCALs of the same parity

A and Z are both taken from the even alcanes or both taken from the odd alcanes.

1 Consecutive ALCALs

They are of type Cnp-C(np+2) or of the type Cni-C(ni+2). The two types have very similar behaviour.

Four cases may be generally distinguished:

First case n≦12; in this case $\epsilon_n$≦0.80 and ΔT≧20° C. (ΔT being the difference between the melting temperatures of the two ALCALs forming the binary).

Miscibility is incomplete; there are eutectics.

Examples

C8–C10: $\epsilon_n$=0.75; ΔT=27.1° C.,

A eutectic is formed for the global composition 82% C8+18% C10

T=−62° C., δ=0, ΔG=190 J/g.

Compositions are obtained which form advantageous PCMMAs for $C8_{1-x}$ $C10_x$ with x≦0.15, more particularly with x=0.05 (T=−57.5° C., δ=2.8, and ΔH=170 J/g)

x=0.11 (T=−59.3° C., δ=1.6, and ΔH=180 J/g).

C10–C12: $\epsilon_n$=0.80, ΔT=20.1° C.: a eutectic is formed for a global composition 80% C10+20% C12 (T=−38° C., δ=0, ΔH=195 J/g).

Second case

12≦n≦18; we then have 0.80≦$\epsilon_n$≦0.88 and 10≦ΔT=<20.

The greater the value of n, the greater the miscibility (in the concentration field) and the narrower the loops will become.

C12–C14: $\epsilon_n$=0.83; ΔT=15.5° C.

Miscibility is extended, but the loops are wide.

Satisfactory alloys are obtained with pure components, more particularly in the C12 direction. (Hereinafter the thermal window δ concerning a concentration range are given with a global attribute taken equal to an integer: 1 when δ≦1, 2 when 1<δ≦2, 4 when 2<δ≦4. On the other hand, for the particular examples δ is given with its true value).

Description of the alloys $C12_{1-x} C14_x$ acceptable according to the invention with 0≦x<0.05: δ=2

0.05≦x<0.15: δ=4, for example x=0.11: T=−12.0° C., δ=3.1, ΔH=175 J/g 0.15≦x≦0.22: δ=2, for example x=0.19: T=−14.2° C., δ=1.7, ΔH=159 J/g 0.92≦x≦1: δ=4, for example x=0.95: T=+5.0° C., δ=3.6, ΔH=205 J/g C13–C15: $\epsilon_n$=0.85; ΔT=15.5° C., miscibility in all proportions is observed, but wide loops, except in the direction of C13.

Description of the acceptable alloys $C13_{1-x} C15_x$:

0≦x<0.20: δ=1

0.20≦x<0.30: δ=2, for example x=0.200: T=−5.1° C., δ=0.9, ΔH=144 J/g 0.30≦x<0.40: δ=4, 0.40≦x<0.95: δ=6, for example x=0.464: T=−0.5° C., δ=6.0, ΔH=148 J/g x=0.794: T=+6.1° C., δ=7.8, ΔH=159 J/g 0.95≦x≦1: δ=4, with doping:

$C13_{0.78}C15_{0.20}C14_{0.02}$: T=−5.0° C., δ=1.0, ΔH=144 J/g $C13_{0.53}C15_{0.45}C14_{0.02}$: T=0.0° C., δ=7.0, ΔH=148 J/g

C14–C16: $\epsilon_n$=0.86; ΔT=12.3° C.,

Whatever the proportions may be, total miscibility is observed when the chains are mixed. The width of the loop varies with the zones.

Amongst the alloys $C14_{1-x} C16_x$, the results obtained are presented with different values of x.

0≦x<0.30: δ=2 for example x=0.10: T=+3.2° C., δ=1.9, ΔH=164 J/g x=0.20: T=+2.9° C., δ=2 ΔH=147 J/g 0.30≦x<0.47: δ=4, for example x=0.35: T=+4.7° C., δ=2.8, ΔH=137 J/g 0.47≦x<0.80: δ=6, for example x=0.60: T=+9.0° C., δ=4.9, ΔH=148 J/g 0.80≦x<0.95: δ=4, for example x=0.90: T=+16.1° C., δ=3.2, ΔH=176 J/g 0.95≦x≦1: δ=2

Formulations of doped C14–C16

$C14_{0.790}C16_{0.200}C15_{0.010}$: T=+2.9° C., δ=2.0, ΔH=159 J/g $C14_{0.890}C16_{0.100}C15_{0.010}$: T=+3.2° C., δ=1.9, ΔH=164 J/g $C14_{0.410}C16_{0.580}C15_{0.010}$: T=+8.8° C., δ=4.9, ΔH=148 J/g $C14_{0.100}C16_{0.890}C15_{0.010}$: T=+16.0° C., δ=3.2, ΔH=175 J/g

C15–C17: $\epsilon_n$=0.57; ΔT=12.0° C.

Total miscibility for $C15_{1-x} C17_x$, but δ is wider to the right of centre.

0≦x<0.20 δ=1

0.20≦x<0.425 δ=2 for example, x=0.30: T=+11.3° C., δ=1.2, ΔH=146 J/g 0.425≦x<0.57 δ=4 for example, x=0.50: T=+14.1° C., δ=2.9, ΔH=156 J/g 0.57≦x<0.80 δ=6 for example, x=0.70: T=+17.0° C., δ=4.4, ΔH=154 J/g 0.80≦x<0.95 δ=4 for example, x=0.90: T=+20.2° C., δ=2.9, ΔH=158 J/g 0.95≦x≦1 δ=2

Doped formulations $C15_{0.685}C17_{0.300}C16_{0.015}$: T=+11.3° C., δ=1.3, ΔH=146 J/g $C15_{0.480}C17_{0.500}C16_{0.020}$: T=+14.0° C., δ=3.0, ΔH=150 J/g $C15_{0.300}C17_{0.690}C16_{0.010}$: T=+17.0° C., δ=4.4, ΔH=154 J/g $C15_{0.100}C17_{0.890}C16_{0.010}$: T=+20.4° C., δ=2.9, ΔH=158 J/g C16–C18: $\epsilon_n$=0.88; ΔT=10.0° C.

All the formulations $C16_{1-x} C18_x$ have δ≦4. The restrictions for 0.03<x<0.10 and 0.75<x<0.97 correspond to widenings of the solid-liquid loop related to interference with solid-solid loops (this phenomenon appears in a number of other binary alloys, whether the pure alcanes themselves have a transition, or whether the transition is induced by the other Cn, as is the case in this binary)

0.10<x<0.50: δ=2

0.50≦x<0.75: δ=4

Doped formulations $C16_{0.690}C18_{0.29}C17_{0.020}$: T=+18.0° C., δ=1.9, ΔH=170 J/g $C16_{0.550}C18_{0.440}C17_{0.010}$: T=+19.8° C., δ=2.0, ΔH=165 J/g Third case 18≦n≦22; in that case we have 0.88<$\epsilon_n$≦0.90 and 7° C.<ΔT<10° C.

Total miscibility; all the molecular alloys have δ≦2; merely a very weak perturbation is felt, due to the possible solid-solid transition (C20 in particular).

C18–C20: $\epsilon_n$=0.89; ΔT=8.6° C.

The following results were obtained with $C18_{1-x} C20_x$:

0≦x<0.03 (doping): δ=1

0.03<x<0.05 with transition effect of C18

0.05<x<0.90: δ=2 for example

| | | |
|---|---|---|
| x = 0.20:T = +28.2° C. | δ = 1.6 | ΔH = 154 J/g |
| x = 0.45:T = +30.6° C. | δ = 1.8 | ΔH = 146 J/g |
| x = 0.80:T = +33.7° C. | δ = 2.0 | ΔH = 150 J/g |

0.90≦x<0.97 with transition effect of C20

0.97≦x<1: δ=1

The following results were obtained with doped binaries:

| | | |
|---|---|---|
| $C18_{0.78} C20_{0.20} C19_{0.02}$ | T = +28.3° C. | δ = 1.8 |
| $C18_{0.78} C20_{0.20} C22_{0.02}$ | T = +28.5° C. | δ = 2.0 |
| $C18_{0.54} C20_{0.45} C19_{0.01}$ | T = +30.8° C. | δ = 1.9 |
| $C18_{0.53} C20_{0.44} C22_{0.03}$ | T = +30.9° C. | δ = 2.0 |
| $C18_{0.19} C20_{0.80} C22_{0.01}$ | T = +33.9° C. | δ = 2.0 |
| $C18_{0.20} C20_{0.79} C19_{0.01}$ | T = +33.9° C. | δ = 2.0 |

We therefore noticed that the doped or undoped binaries C18–C20 respond substantially in the same manner. Thus, the doping of a given PCMMA enables T to be adjusted without affecting δ (or ΔH) for a value of x.

C19–C21: $\epsilon_n$=0.89; ΔT=8.4° C.

$C19_{1-x}\ C21_x$

0≦x<0.20: δ=1

0.20≦x<0.90: δ=2

0.90≦x≦1: δ=1

With doping (example)

$C19_{0.290}C21_{0.690}C20_{0.020}$: T=+35.5° C., δ=1.2 ΔH=151 J/g

C20–C22: $\epsilon_n$=0.90, ΔT=7.6° C.

We note that the loop becomes thinner in comparison with those of the preceding alloys. A solid-solid transition effect of C20 is observed only between 0.02<x<0.05.

With x<0.40, we obtain δ=1

0.40≦x<0.75: δ=2

0.75≦x≦1: δ=1

Examples of doped formulations, classified by T (the ΔH are practically equal to 147 J/g)

| | | |
|---|---|---|
| $C20_{0.794}C22_{0.200}C19_{0.004}C21_{0.002}$ | T = +37.6° C. | δ = 0.8 |
| $C20_{0.80}C22_{0.17}C21_{0.03}$ | T = +37.8° C. | δ = 0.8 |
| $C20_{0.78}C22_{0.20}C24_{0.02}$ | T = +38.0° C. | δ = 0.8 |
| $C20_{0.48}C22_{0.49}C21_{0.03}$ | T = +39.7° C. | δ = 1.5 |
| $C19_{0.003}C20_{0.471}C21_{0.002}C22_{0.524}$ | T = +39.8° C. | δ = 1.3 |
| $C20_{0.50}C22_{0.48}C24_{0.02}$ | T = +40.0° C. | δ = 1.5 |
| $C19_{0.002}C20_{0.376}C21_{0.002}C22_{0.620}$ | T = +40.3° C. | δ = 1.2 |
| $C20_{0.38}C22_{0.60}C24_{0.02}$ | T = +40.6° C. | δ = 1.4 |
| $C20_{0.30}C22_{0.69}C21_{0.01}$ | T = +41.2° C. | δ = 1.4 |
| $C19_{0.002}C20_{0.279}C21_{0.002}C22_{0.717}$ | T = +41.3° C. | δ = 1.2 |
| $C19_{0.001}C20_{0.184}C21_{0.003}C22_{0.812}$ | T = +42.0° C. | δ = 0.9 |
| $C20_{0.09}C22_{0.90}C21_{0.01}$ | T = +42.8° C. | δ = 0.9 |
| $C19_{0.001}C20_{0.093}C21_{0.003}C22_{0.903}$ | T = +42.9° C. | δ = 1.0 |

C21–C23: $\epsilon_n$=0.90; ΔT=7.1° C.

$C21_{1-x}\ C23_x$

0≦x≦0.35: δ=1

0.35<x<0.60: δ=2

0.60≦x≦1: δ=1

Doped formulations $C21_{0.580}C23_{0.400}C22_{0.020}$: T=43.3° C., δ=1.3, ΔH=152 J/g Fourth Case n≧22 $\epsilon_n$>0.90 ΔT<7° C.

From C22–C24 inclusive, all the binaries have total miscibilities with δ=1, whatever the value of x may be. The same thing applies to the doped binaries. The following are a few examples of doped binaries, compementary examples being given in Table 2.

C22–C24: $\epsilon_n$=0.91; ΔT=6.5° C.

| | | | |
|---|---|---|---|
| $C22_{0.70}\ C24_{0.28}\ C20_{0.02}$ | T = +45.2° C., | δ = 0.8, | +800 H = 153 J/g |
| $C22_{0.68}\ C24_{0.30}\ C26_{0.02}$ | T = +45.7° C., | δ = 0.8, | +800 H = 153 J/g |
| $C22_{0.30}\ C24_{0.68}\ C20_{0.02}$ | T = +48.1° C., | δ = 0.9, | +800 H = 155 J/g |
| $C22_{0.28}\ C24_{0.70}\ C23_{0.02}$ | T = +48.4° C., | δ = 0.9 | +800 H = 156 J/g |

C23–C25: $\epsilon_n$=0.91; ΔT=6.1° C.

$C23_{0.100}C25_{0.890}C24_{0.010}$: T=+53.0° C., δ=0.9, ΔH=161 J/g

C24–C26: $\epsilon_n$=0.92; ΔT=5.5° C.

$C24_{0.90}C26_{0.08}C20_{0.02}$: T=+50.2° C., δ=0.4, ΔH=158 J/g $C24_{0.49}C26_{0.50}C20_{0.001}$: T=+52.2° C., δ=0.9, ΔH=158 J/g $C24_{0.49}C26_{0.50}C22_{0.01}$: T=+53.5° C., δ=0.19, ΔH=162 J/g

If n continues to increase, alloys can readily be obtained in which δ is lower than 0.5 even for the central concentrations, whatever x may be. The following are two examples:

C30–C32: $\epsilon_n$=0.93; ΔT=3.9° C.

δ≦0.5 for every x of $C30_{1-x}\ C32_x$

Example $C30_{0.50}C32_{0.50}$ T=+67.0° C., δ=0.2, ΔH=160 J/g

C44–C46: $\epsilon_n$=0.95; ΔT=1.6° C.

δ<0.5 for every x of $C44_{1-x}\ C46_x$

Example $C44_{0.50}C46_{0.50}$ T=+87.4° C., δ=0.2, ΔH=220 J/g

2) Non-consecutive ALCALs

First case: type Cnp C(np+4) and type Cni C(ni+4)

We find substantially the same evolution as for the consecutive ALCALs with an increase in the extent of the zones of miscibility and an improvement in the quality of the thermal window as n increases and ΔT diminishes, the latter parameter being determining.

$\epsilon_n$≧0.80 is necessary to have miscibility in all proportions. Moreover, we must have ΔT≦10° C. for all the alloys to have δ≦2. $\epsilon_n$≧0.90 is necessary for all the alloys to have their δ≦1.

Examples of formulations

C18–C22: $\epsilon_n$=0.78; ΔT=16.2° C.

$C18_{(1-x)}C22_x$ acceptable for 0.05<x≦0.20 with δ=2 0.20<x≦0.40 with δ=4 0.90≦x≦1 with δ=4

$C18_{0.870}C22_{0.100}C20_{0.030}$: T=+27.8 δ=1.8, ΔH=164 J/g $C18_{0.700}C22_{0.280}C20_{0.020}$: T=+30.8 δ=3.9, ΔH=139 J/g

C22–C26: $\epsilon_n$=0.82; ΔT=12.0° C.

$C22_{(1-x)}C26_x$ acceptable for 0≦x≦0.35 with δ=2 0.35<x<0.75 with δ=4 0.75≦x≦1 with δ=2

$C22_{0.500}C26_{0.490}C24_{0.010}$: T=+50.2° C., δ=2.6, ΔH=157 J/g

C28–C32: $\epsilon_n$=0.86; T=8.3° C.

$C28_{(1-x)}C32_x$ acceptable for 0≦x≦0.30 with δ=1 0.30<x≦0.90 with δ=2 0.90<x≦1 with δ=1

$C28_{0.790}C32_{0.200}C30_{0.010}$: T=+62.4° C., δ=0.4, ΔH=160 J/g

C46–C50: $\epsilon_n$=0.91; ΔT=4.1° C.

δ=1 whatever the content may be $C46_{0.100}C50_{0.890}C44_{0.010}$: T=+91.9° C. δ=0.6, ΔH=215 J/g 2nd case: type Cnp C(np+k) and type Cni C(ni+k) where k is an even number greater than 4.

To obtain fairly extensive ranges of miscibility with good δs, use is made of relatively high nps (or nis), so as to have simultaneously $\epsilon_n$>0.80 and ΔT<10° C.

Examples of binaries with k=6

C26–C32: $\epsilon_n$=0.77; ΔT=13.3° C.

Total miscibility, but the loop is wide in the direction of C32. As a result, we have:

$C26_{(1-x)}\ C32_x$ acceptable for 0≦x≦0.10 with δ=1 0.10<x≦0.25 with δ=2 0.25<x≦0.45 with δ=4 0.90≦x≦1 with δ=4

$C26_{0.800}C32_{0.190}C30_{0.010}$: T=+57.3° C., δ=2.0, ΔH=160 J/g

C44–C50: $\epsilon_n=0.86$; $\Delta T=5.7°$ C.

C44$_{(1-x)}$C50$_x$ acceptable for every x for $0 \leq x \leq 0.32$ with $\delta=1$ $0.32<x<0.75$ with $\delta=2$ $0.75 \leq x \leq 1$ with $\delta=1$ C44$_{0.395}$C50$_{0.585}$C46$_{0.005}$C48$_{0.015}$: T=+89.2° C., $\delta=1.5$, $\Delta H=225$ J/g If the nps or nis are low and/or if k is high, acceptable solutions will be obtained in the form of eutectic mixtures of alloys (with $\delta$s therefore not differing much from 0° C.). For example, C23–C33: $\epsilon_n=0.57$; $\Delta T=23.7°$ C.

Eutectic at T +46° C.

II Binary ALCALs with different parity

One of A and B belongs to the even alcanes, the other to the odd alcanes, or vice verse.

1) Consecutive ALCALs

They are of type Cnp/Cni with i=p+1 or Cni/Cnp with p=i+1.

As in the preceding cases, in fact a favourable effect is observed from the lengthening of the chain. Nevertheless, in this case consideration must be given to the effect of non-isomorphism which characterizes the pairs Cnp/Cni or Cni/Cnp, as long as the ns are less than 21. Two cases can therefore be distinguished:

First case

At lease one of the constituents has n<21. In this case miscibility could not be total, but as soon as the Ens are higher than 0.90, for each binary, two relatively narrow partial loops are observed which intersect one another in a zone excluded according to the invention from the point of view of $\delta$, a zone systematically shifted in the direction of the even Cn.

Examples of binaries

C12–C13: $\epsilon_n=0.92$; $\Delta T=4.1°$ C.

We have acceptable alloys C12$_{(1-x)}$C13$_x$ as soon as $x \geq 0.30$ $0.30 \leq x<0.90$ avec $\delta=4$ $0.90 \leq x \leq 1$ avec $\delta=2$ with more particularly:
the following undoped formulations:

C12$_{0.700}$C13$_{0.300}$: T=−13.6° C., $\delta=2.6$, $\Delta H=146$ J/g

C12$_{0.500}$C13$_{0.500}$: T=−11.4° C., $\delta=2.2$, $\Delta H=146$ J/g the following doped formulations:

C12$_{0.690}$C13$_{0.300}$C11$_{0.010}$: T=−13.5° C., $\delta=2.7$, $\Delta H=146$ J/g C12$_{0.480}$C13$_{0.480}$C11$_{0.040}$: T=−11.8° C., $\delta=2.2$, $\Delta H=146$ J/g C12$_{0.200}$C13$_{0.780}$C11$_{0.020}$: T=−8.0° C., $\delta=2.4$, $\Delta H=150$ J/g C13–C14: $\epsilon_n=0.92$, $\Delta T=11.4°$ C.

We have alloys C13$_{(1-x)}$C14$_x$ where $x \leq 0.50$ $0 \leq x<0.07$ with $\delta=1$ $0.07 \leq x \leq 0.50$ with $\delta=2$ with more particularly
as undoped formulations:

C13$_{0.700}$C14$_{0.300}$: T=−3.8° C., $\delta=1.2$, $\Delta H=153$ J/g

C13$_{0.500}$C14$_{0.500}$: T=−2.3° C., $\delta=1.7$, $\Delta H=152$ J/g as doped formulations:

C13$_{0.690}$C14$_{0.300}$C15$_{0.010}$: T=−3.9° C., $\delta=1.4$, $\Delta H=152$ J/g C13$_{0.485}$C14$_{0.490}$C15$_{0.025}$: T=−2.5° C., $\delta=1.8$, $\Delta H=152$ J/g C14–C15: $\epsilon_n=0.93$, $\Delta T=4.1°$ C.

We have alloys C14$_{(1-x)}$C15$_x$ when $x>0.20$ $0.20<x<0.70$ with $\delta=4$ $0.70 \leq x<0.90$ with $\delta=2$ $0.90 \leq x \leq 1$ with $\delta=1$ Examples of doped formulations C14$_{0.400}$C15$_{0.570}$C13$_{0.030}$: T=+5.2° C., $\delta=3.9$, $\Delta H=147$ J/g C14$_{0.260}$C15$_{0.700}$C16$_{0.040}$: T=+7.7° C., $\delta=2.0$, $\Delta H=155$ J/g C15–C16: $\epsilon_n=0.93$, $\Delta T=8.2°$ C.

We have alloys C15$_{(1-x)}$C16$_x$ except if $0.70<x<0.90$ $0 \leq x \leq 0.25$ with $\delta=1$ $0.25<x \leq 0.70$ with $\delta=2$ $0.90 \leq x \leq 1$ with $\delta=4$ Examples of doped formulations C15$_{0.840}$C16$_{0.130}$C14$_{0.030}$: T=+9.5° C., $\delta=1.0$, $\Delta H=153$ J/g C15$_{0.840}$C16$_{0.150}$C14$_{0.010}$: T=+10.5° C., $\delta=0.8$, $\Delta H=150$ J/g C15$_{0.690}$C16$_{0.300}$C14$_{0.010}$: T=+11.2° C., $\delta=1.3$, $\Delta H=156$ J/g C16–C17: $\epsilon_n=0.94$, $\Delta T=3.8°$ C.

We have alloys C16$_{(1-x)}$C17$_x$ si $x>0.10$ $0.10<x \leq 0.40$ with $\delta=1$ $0.40<x \leq 0.90$ with $\delta=2$ $0.90<x \leq 1$ with $\delta=1$ Examples of doped formulations C16$_{0.300}$C17$_{0.685}$C15$_{0.010}$C18$_{0.005}$: T=19.8° C., $\delta=1.5$, $\Delta H=160$ J/g C16$_{0.100}$C17$_{0.885}$C15$_{0.005}$C18$_{0.010}$: T=21.3° C., $\delta=1.1$, $\Delta H=165$ J/g C17–C18: $\epsilon_n=0.94$; $\Delta T=6.4°$ C.

We have alloys C17$_{(1-x)}$C18$_x$ for $x<0.75$ $0 \leq x \leq 0.50$ with $\delta=1$ $0.50<x<0.75$ with $\delta=2$ Example of doped formulation C17$_{0.300}$C18$_{0.690}$C19$_{0.010}$: T=+25.7° C., $\delta=1.2$, $\Delta H=159$ J/g C19–C20: $\epsilon_n=0.95$; $\Delta T=4.7°$ C.

We have alloys C19$_{(1-x)}$C20$_x$ avec $\delta<1$ whatever may be, x except between $0.90<x<1$ Example of doped formulation C19$_{0.300}$C20$_{0.680}$C21$_{0.020}$: T=+35.2° C., $\delta=0.9$, $\Delta H=151$ J/g Second case: All the constituents have n>21

Since the phases are isomorphic prior to melting of the even and odd alcanes, total miscibility is possible and actually occurs, more particularly since the $\epsilon_n$s are higher than or equal to 0.95.

C21–C22: $\epsilon_n=0.95$; $\Delta T=3.9°$ C.

All the alloys C21$_{(1-x)}$C22$_x$ are acceptable with $\delta<1$.

Example of doped formulation

C21$_{0.490}$C22$_{0.490}$C23$_{0.020}$: T=+41.8° C., $\delta=0.6$, $\Delta H=150$ J/g C22–C23: $\epsilon_n=0.95$; $\Delta T=3.2°$ C.

All the alloys C22$_{(1-x)}$C23$_x$ are acceptable with $\delta<1$.

Example of doped formulation

C22$_{0.490}$C23$_{0.500}$C24$_{0.010}$: T=+45.7° C., $\delta=0.5$, $\Delta H=155$ J/g C24–C25: $\epsilon_n=0.96$; $\Delta T=2.8°$ C.

Example of doped formulation

C24$_{0.500}$C25$_{0.490}$C26$_{0.010}$: T=+51.7° C., $\delta=0.4$, $\Delta H=159$ J/g C35–C36: $\epsilon_n$=0.97; ΔT=1.1° C.

Example of doped formulation $C35_{0.890}C36_{0.090}C37_{0.020}$: T=+75.2° C., δ=0.4, ΔH=160 J/g 2) Non-consecutive ALCALs If wide ranges of acceptable concentrations are desired, components with $\epsilon_n$ higher than 0.90 should be selected, or eutectic mixtures of alloys with low $\epsilon_n$s can be used.

Example

C15–C22: $\epsilon_n$=0.53; ΔT=34.4° C.

Eutectic at T +9° C.

EXAMPLE 5

ALCAL ternaries a) Study of evolutionn.

The ternaries will be presented in the following manner; Cn1-Cn2-Cn3 with n1<n2<n3, also corresponding to the increased order of the melting temperature.

For each ternary the $\epsilon_n$s will be given for the components taken in pairs in the following order: Cn1-Cn2; Cn2-Cn3 and Cn1-Cn3. This third value will always be the lowest, having regard to the system adopted.

1) Ternary with all consecutive Cns: These are ternaries Cn-C(n+1)-C(n+2)

The following will be mentioned by way of example:

| Cn1 Cn2 Cn3 | $\epsilon_{1,2}$ | $\epsilon_{2,3}$ | $\epsilon_{1,3}$ |
|---|---|---|---|
| C14 – C15 – C16 | 0.93 | 0.93 | 0.86 |
| C15 – C16 – C17 | 0.93 | 0.94 | 0.87 |
| C20 – C21 – C22 | 0.95 | 0.95 | 0.90 |
| C22 – C23 – C24 | 0.95 | 0.96 | 0.91 |

The extent of the acceptable ranges of concentrations increases as the different $\epsilon_{1,2}$; $\epsilon_{2,3}$ et $\epsilon_{1,3}$ increase. For the system C14-C15-C16 and C15-C16-C17 where $\epsilon_{1,3}$<0.90, the quality ranges δ=1 and δ=2 are not very extensive, and levels exist where δ>4. If all the $\epsilon_n$=0.90, all the formulations have at least the attributes δ≦2 (case of C20-C21-C22, except for a small zone disturbed by the solid-solid transition of C20) and even the attribute δ≦1 (case of C22-C23-C24).

2) Ternaries with not directly consecutive Cns

First general case: ternaries Cn-C(n+2)-C(n+4).

There are, for example, the following ternaries (3 cases of which are given in detail hereinafter).

| Cn1 – Cn2 – Cn3 | $\epsilon_{1,2}$ | $\epsilon_{2,3}$ | $\epsilon_{1,3}$ |
|---|---|---|---|
| C18 – C20 – C22 | 0.89 | 0.90 | 0.78 |
| C20 – C22 – C24 | 0.90 | 0.91 | 0.80 |
| C21 – C23 – C25 | 0.90 | 0.91 | 0.81 |
| C22 – C24 – C26 | 0.91 | 0.92 | 0.82 |

The same phenomenon is found as previously: increase in the extent of the levels with the better attribute with an increase in the three $\epsilon_n$ concerned, $\epsilon_{1,3}$ being the most decisive, since it brings into play the two Cns furthest away in the length of the chain.

Second general case

In proportion as the distances between the various Cns concerned are greater, the greater the increase must be in the scale of the alcanes, classified by their n, to obtain important levels of ALCALs having a satisfactory δ. The following are two complete examples:

| | | | |
|---|---|---|---|
| C20 – C22 – C26 | 0.90 | 0.82 | 0.70 |
| C44 – C46 – C50 | 0.95 | 0.91 | 0.86 |

If for the first one there are wide ranges of formulations with the attribute δ=6, in contrast for the second one, the majority of the formulations have a attribute δ=1 and the others have a 1<δ≦2.

With a reduction in the case of the ns and/or if the distance between the Cns is increased, eutectic mixtures of alloys can moreover be generated.

b): Examples

1. Study of the ternary ALCALs xC14-yC15-zC16

FIG. 1 is a diagram giving the attributes of the different alloys. The diagram shows eight zones (surfaces numbered $S_1$ to $S_8$).

One zone where δ≦1: $S_1$

Definition of the zone $S_1$ $$\begin{cases} 18x - 2y + 3z \leq 0 \\ y \geq 0.75 \\ x + y + z = 1 \end{cases}$$

with more particularly the following examples:

$x = 0.03$  $y = 0.84$  $z = 0.13$  $T_\delta = +9.5_{1.0}$ $x = 0.01$  $y = 0.84$  $z = 0.15$  $T_\delta = +10.5_{0.8}$ Two zones where 1<δ2: $S_2$ and $S_3$ Definition of the zone $S_2$=S not including $S_1$ where $$S \begin{cases} 49x - 21y + 9z \leq 0 \\ x + y + z = 1 \end{cases}$$

with more particularly the following examples:

$x = 0.01$  $y = 0.49$  $z = 0.50$  $T_\delta = +12.3_{1.7}$ $x = 0.01$  $y = 0.69$  $z = 0.30$  $T_\delta = +11.2_{1.3}$ $x = 0.07$  $y = 0.56$  $z = 0.37$  $T_\delta = +10.7_{2.0}$ $x = 0.26$  $y = 0.67$  $z = 0.07$  $T_\delta = +7.7_{2.0}$ Definition of the zone $S_3$ $$\begin{cases} x \geq 0.7 \\ 3y - 5z \leq 0 \\ x - 4y - z \geq 0 \\ x + y + z = 1 \end{cases}$$

with more particularly the following examples:

$x = 0.73$  $y = 0.14$  $z = 0.13$  $T_\delta = +3.6_{2.0}$ $x = 0.89$  $y = 0.01$  $z = 0.10$  $T_\delta = +3.2_{1.9}$ -continued $x = 0.79$ $y = 0.01$ $z = 0.20$ $T_\delta = +2.9_{2.0}$ Two zones where $2 < \delta \leq 4$: $S_4$ and $S_5$
Definition of $S_4$ $$\begin{cases} 4x + 29y - z \leq 0 \\ x + y + z = 1 \end{cases}$$

with more particularly the following example:

$x = 0.10$ $y = 0.01$ $z = 0.89$ $T_\delta = +16.0_{3.2}$

Definition of $S_5$ total triangle excluding: $S_1 S_2 S_3 S_4 S_6 S_7$ and $S_8$ with more particularly the following examples:

$x = 0.14$ $y = 0.23$ $z = 0.63$ $T_\delta = +11.9_{3.1}$ $x = 0.21$ $y = 0.56$ $z = 0.23$ $T_\delta = +8.5_{2.3}$ $x = 0.24$ $y = 0.33$ $z = 0.43$ $T_\delta = +9.5_{3.9}$ $x = 0.43$ $y = 0.33$ $z = 0.24$ $T_\delta = +6.5_{2.6}$ $x = 0.57$ $y = 0.17$ $z = 0.26$ $T_\delta = +5.3_{2.6}$ $x = 0.64$ $y = 0.01$ $z = 0.35$ $T_\delta = +4.7_{2.8}$ Two zones where $4 < \delta \leq 6$: $S_6$ et $S_7$
Definition of $S_6$ $$\begin{cases} x \geq 0.2 \\ y \leq 0.3 \\ 19x + 9y - 21z \leq 0 \\ x + y + z = 1 \end{cases}$$

with more particularly the following examples:

$x = 0.33$ $y = 0.07$ $z = 0.60$ $T_\delta = +9.9_{4.4}$ $x = 0.41$ $y = 0.01$ $z = 0.58$ $T_\delta = +8.8_{4.9}$ $x = 0.32$ $y = 0.24$ $z = 0.44$ $T_\delta = +8.8_{4.4}$ Definition of $S_7$ $$\begin{cases} x - 4y - z \geq 0 \\ 3y - 5z \geq 0 \\ x + y + z = 1 \end{cases}$$

One zone where $\delta < 6$: $S_8$
Definition of $S_8$ $$\begin{cases} x \leq 0.2 \\ z \geq 0.7 \\ 4x + 29y - z > 0 \end{cases}$$

-continued $$\begin{cases} x + y + z = 1 \end{cases}$$

with more particularly the following example:

$x = 0.17$ $y = 0.07$ $z = 0.76$ $T_\delta = +13.8_{7.4}$

2. Study of the ternary ALCALs xC15-yC16-zC17

Figure 2:
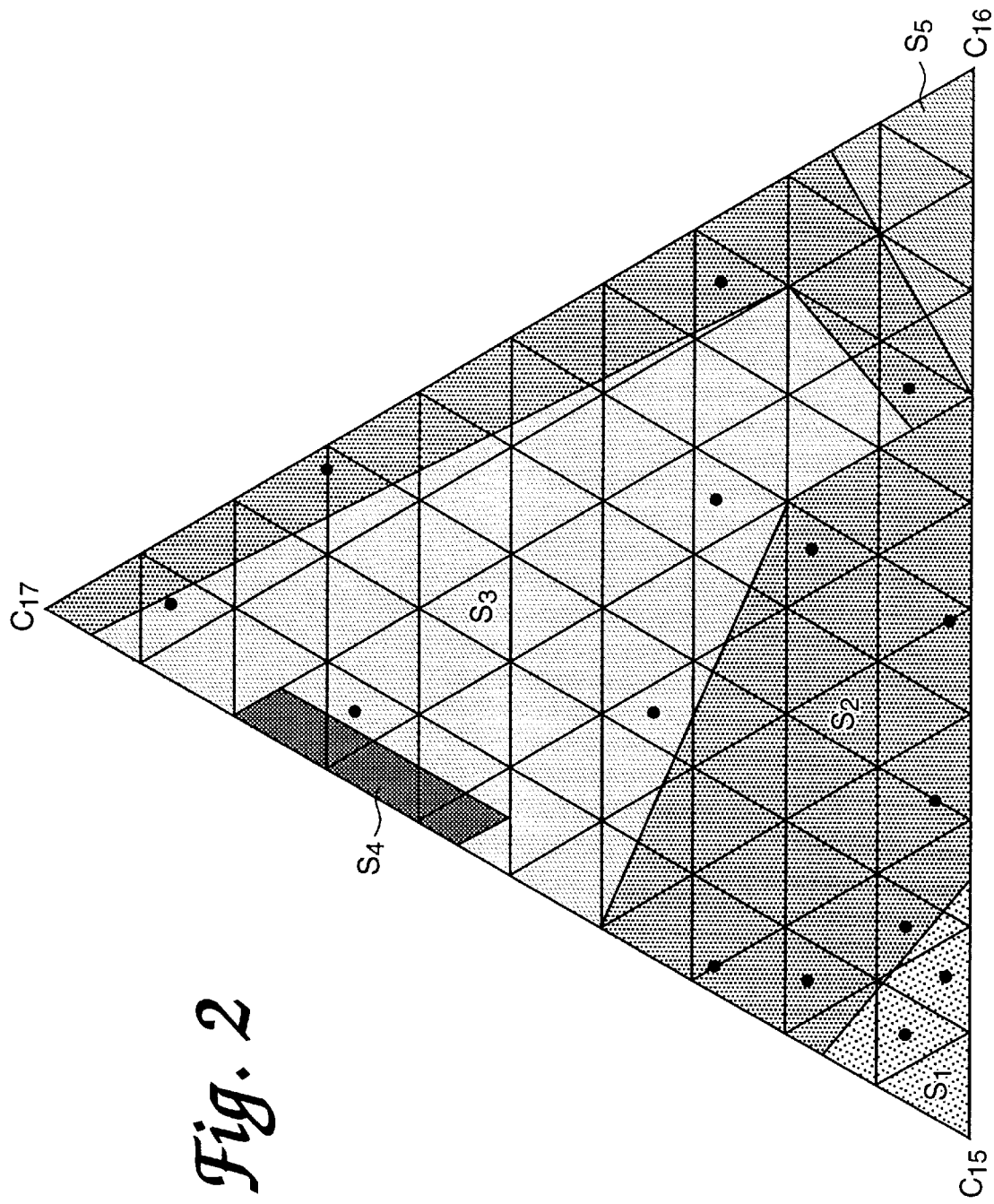

FIG. 2 is a diagram giving the attributes of the different alloys.

Five zones are distinguished (surfaces numbered from $S_1$ to $S_5$).

A zone where $\delta \leq 1$: $S_1$
Definition of $S_1$ $$\begin{cases} 3x + 9y - 17z \geq 0 \\ x + y + z = 1 \end{cases}$$

with more particularly the following examples:

$x = 0.83$ $y = 0.15$ $z = 0.02$ $T_\delta = +10.6_{0.8}$ $x = 0.87$ $y = 0.07$ $z = 0.06$ $T_\delta = +10.3_{1.0}$ A zone where $1 < \delta \leq 2$: $S_2$
Definition of $S_2$ total triangle excluding $S_1 S_3 S_4 S_5$ with more particularly the following examples:

$x = 0.77$ $y = 0.17$ $z = 0.06$ $T_\delta = +10.8_{1.3}$ $x = 0.77$ $y = 0.07$ $z = 0.16$ $T_\delta = +10.9_{1.4}$ $x = 0.67$ $y = 0.30$ $z = 0.03$ $T_\delta = +11.4_{1.4}$ $x = 0.50$ $y = 0.48$ $z = 0.02$ $T_\delta = +12.4_{1.7}$ $x = 0.36$ $y = 0.47$ $z = 0.17$ $T_\delta = +13.5_{2.0}$ $x = 0.27$ $y = 0.66$ $z = 0.07$ $T_\delta = +14.9_{2.0}$ $x = 0.70$ $y = 0.03$ $z = 0.27$ $T_\delta = +11.4_{1.4}$ $x = 0.06$ $y = 0.67$ $z = 0.27$ $T_\delta = +16.5_{1.9}$ $x = 0.03$ $y = 0.27$ $z = 0.70$ $T_\delta = +19.5_{1.6}$ One zone where $2 < \delta \leq 4$: $S_3$
Definition of the zone $S_3$: S not including $S_5$ $$\begin{cases} 133x - 17y - 7z \geq 0 \\ 6x - 4y + 11z \geq 0 \\ 2x - 3z \leq 0 \\ x \leq 0.3 \\ x + y + z = 1 \end{cases}$$

with more particularly the following examples:

$x = 0.44$ $y = 0.23$ $z = 0.33$ $T_\delta = +14.1_{2.6}$ $x = 0.27$ $y = 0.47$ $z = 0.26$ $T_\delta = +14.8_{2.3}$ -continued $x = 0.27 \quad y = 0.07 \quad z = 0.66 \quad T_\delta = +17.1_{3.9}$ $x = 0.06 \quad y = 0.07 \quad z = 0.87 \quad T_\delta = +20.4_{2.5}$ Two zones where $\delta > 4$: $S_4$ and $S_5$ Definition of $S_4$ $$\begin{cases} 0.2 \leq x \leq 0.45 \\ 0 \leq y \leq 0.05 \\ 0.5 \leq z \leq 0.8 \\ x + y + z = 1 \end{cases}$$

with more particularly the following example:

$x = 0.40 \quad y = 0.02 \quad z = 0.58 \quad T_\delta = +15.8_{4.3}$

Definition of $S_5$ $$\begin{cases} 7x - 3y + 17z \leq 0 \\ x + y + z = 1 \end{cases}$$

with more particularly the following example:

$x = 0.10 \quad y = 0.88 \quad z = 0.02 \quad T_\delta = +17.0_{4.2}$

3: Study of the ternary ALCALs xC20-yC21-zC22

Figure 3:
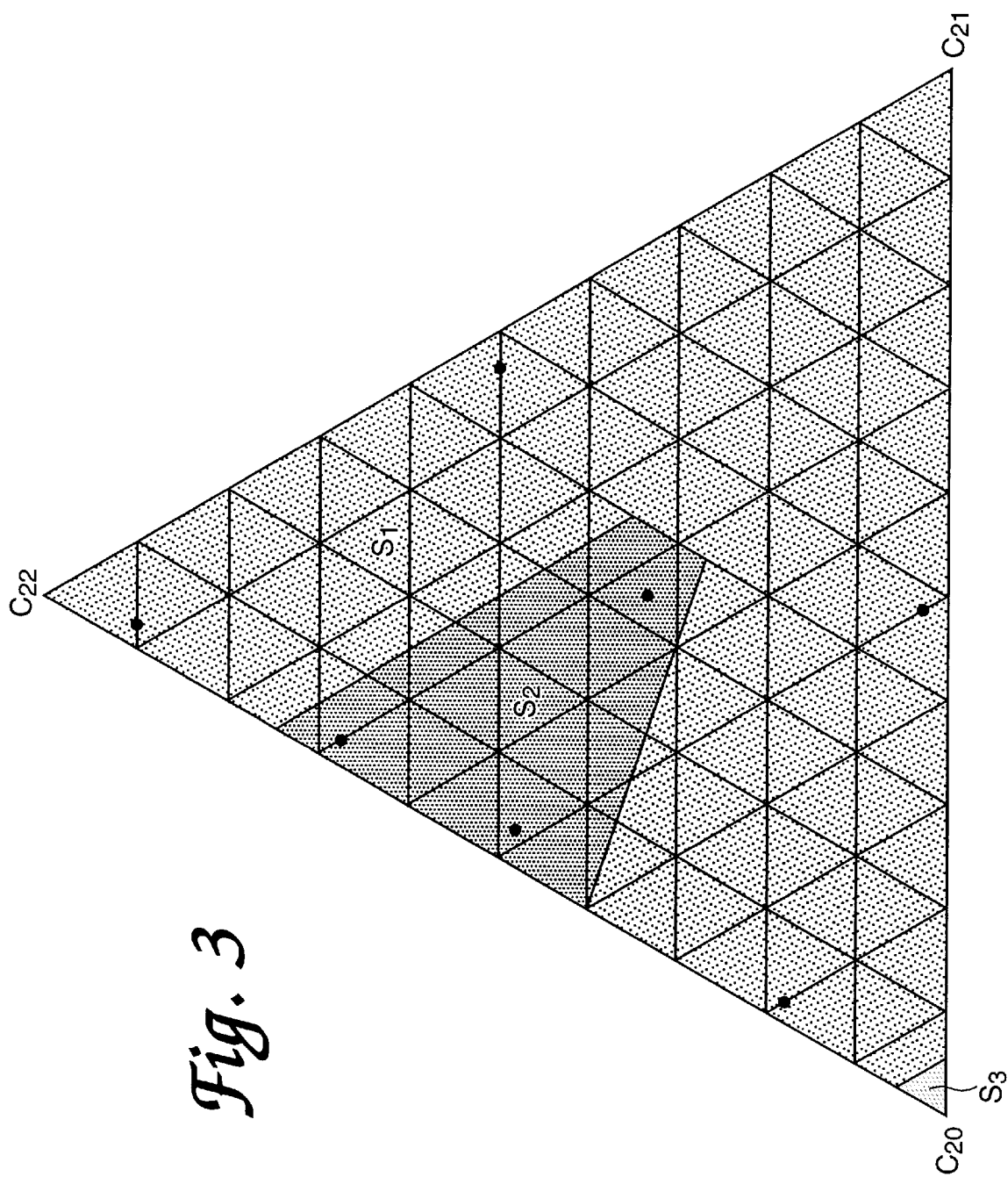

FIG. 3 is a diagram showing the attributes of the different alloys. Three zones can be distinguished (surfaces numbered from $S_1$ to $S_3$)

One zone where $\delta \leq 1$: $S_1$

Definition of the zone $S_1$ total triangle excluding $S_2$ and $S_3$ with more particularly the following examples:

$x = 0.09 \quad y = 0.01 \quad z = 0.90 \quad T_\delta = +42.8_{0.9}$ $x = 0.50 \quad y = 0.47 \quad z = 0.03 \quad T_\delta = +38.2_{0.6}$ $x = 0.80 \quad y = 0.03 \quad z = 0.17 \quad T_\delta = +37.5_{0.8}$ $x = 0.03 \quad y = 0.47 \quad z = 0.50 \quad T_\delta = +41.6_{0.6}$ A zone where $1 < \delta \leq 2$: $S_2$ Definition of the zone $S_2$ $$\begin{cases} 3x - y - z \geq 0 \\ 2x - 3y + 2z \geq 0 \\ 6x + y - 9z \leq 0 \\ x + y + z = 1 \end{cases}$$

$x = 0.30 \quad y = 0.01 \quad z = 0.69 \quad T_\delta = +41.2_{1.4}$ $x = 0.48 \quad y = 0.03 \quad z = 0.49 \quad T_\delta = +39.7_{1.5}$ $x = 0.33 \quad y = 0.34 \quad z = 0.33 \quad T_\delta = +39.5_{1.3}$ A zone where $\delta > 4$: $S_3$ Definition of the zone $S_3$ $$\begin{cases} x \geq 0.95 \\ x + y + z = 1 \end{cases}$$

4: Study of the ternary ALCALs xC22-yC23-zC24

Figure 4:
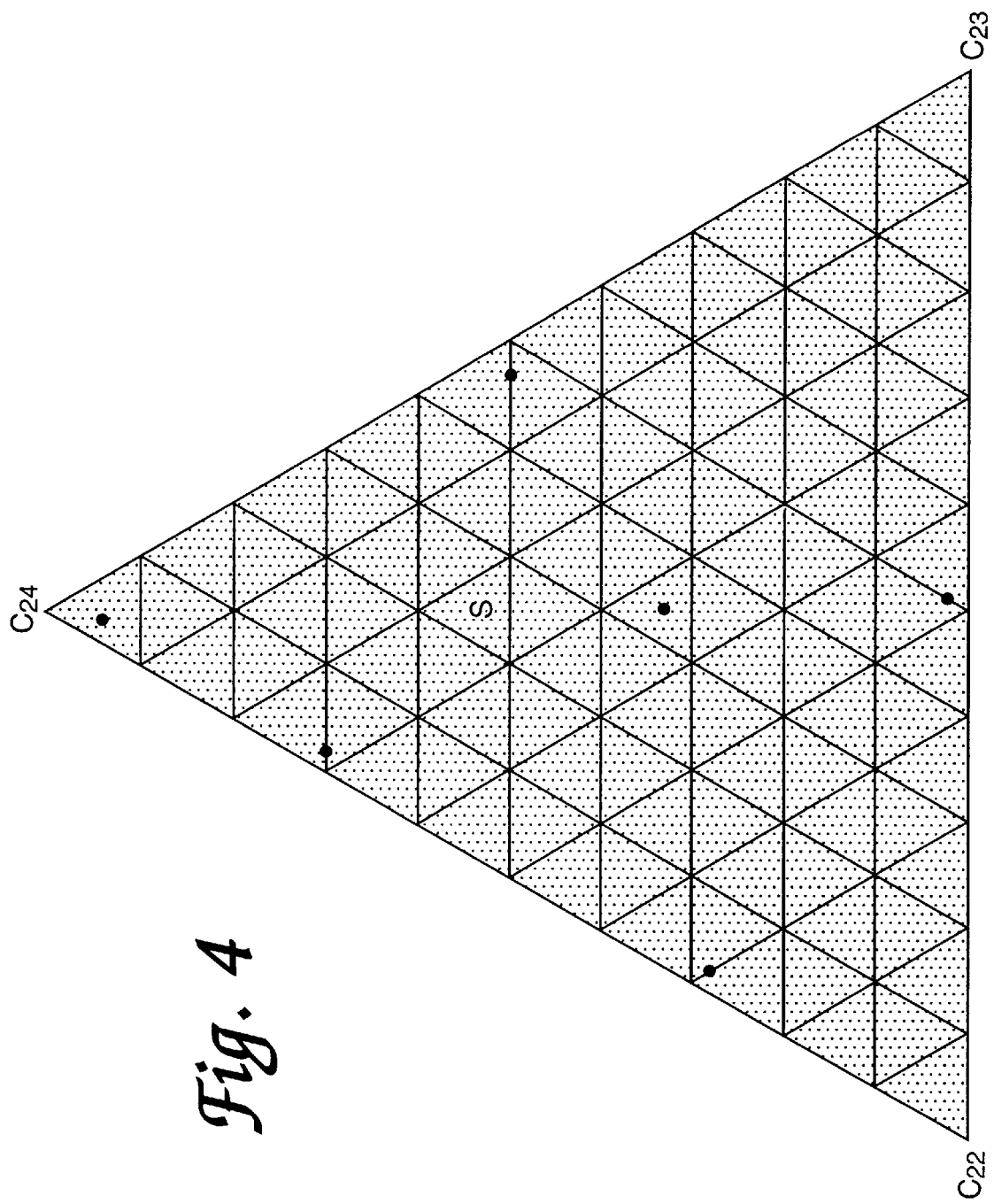

The diagram of the attributes of the different alloys shown in FIG. 4 is characterized by the existence of a single zone called S where $\delta \leq 1$ Definition of the zone S: the whole ternary, that is $x+y+z=1$ with more particularly the following examples:

$x = 0.05 \quad y = 0.02 \quad z = 0.93 \quad T_\delta = +50.2_{0.4}$ $x = 0.28 \quad y = 0.02 \quad z = 0.70 \quad T_\delta = +48.4_{0.9}$ $x = 0.33 \quad y = 0.34 \quad z = 0.33 \quad T_\delta = +47.1_{0.7}$ $x = 0.70 \quad y = 0.02 \quad z = 0.28 \quad T_\delta = 45.7_{0.9}$ $x = 0.48 \quad y = 0.50 \quad z = 0.02 \quad T_\delta = 45.8_{0.6}$ $x = 0.03 \quad y = 0.47 \quad z = 0.50 \quad T_\delta = 48.9_{0.5}$ 5: Study of the ternary ALCALs xC18-yC20-zC22

Figure 5:
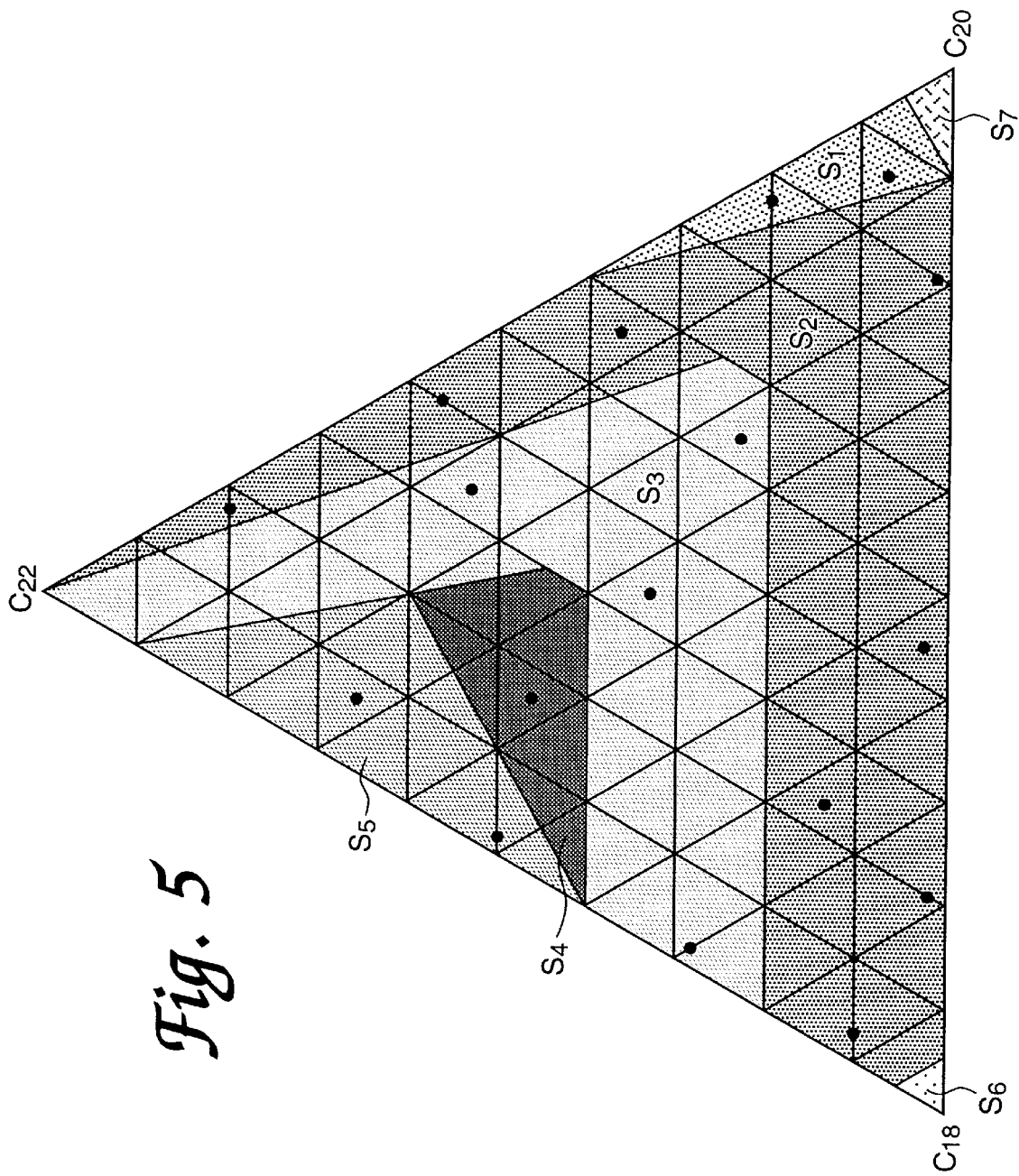

FIG. 5 is a diagram showing the attributes of the different alloys. Seven zones can be distinguished (surfaces numbered from $S_1$ to $S_7$).

One zone where $\delta \leq 1$: $S_1$

Definition of the zone $S_1$: S not including $S_7$ $$\begin{cases} 18x - 2y + 3z \leq 0 \\ x + y + z = 1 \end{cases}$$

with more particularly the following examples:

$x = 0.06 \quad y = 0.88 \quad z = 0.06 \quad T_\delta = +36.1_{1.0}$ $x = 0.03 \quad y = 0.77 \quad z = 0.20 \quad T_\delta = +37.5_{0.9}$ One zone where $1 < \delta \leq 2$: $S_2$ Definition of the zone $S_2$: total triangle excluding $S_1$, $S_3$, $S_4$, $S_5$, $S_6$ and $S_7$ with more particularly the following examples:

$x = 0.78 \quad y = 0.20 \quad z = 0.02 \quad T_\delta = +28.5_{2.0}$ $x = 0.53 \quad y = 0.44 \quad z = 0.03 \quad T_\delta = +30.9_{2.0}$ $x = 0.19 \quad y = 0.80 \quad z = 0.01 \quad T_\delta = +33.9_{2.0}$ $x = 0.63 \quad y = 0.24 \quad z = 0.13 \quad T_\delta = +30.0_{1.9}$ $x = 0.06 \quad y = 0.56 \quad z = 0.38 \quad T_\delta = +37.8_{1.3}$ $x = 0.40 \quad y = 0.58 \quad z = 0.02 \quad T_\delta = +40.1_{1.5}$ $x = 0.18 \quad y = 0.80 \quad z = 0.02 \quad T_\delta = +41.8_{1.1}$ $x = 0.87 \quad y = 0.10 \quad z = 0.03 \quad T_\delta = +27.8_{1.8}$ One zone where $2 < \delta \leq 4$: $S_3$ Definition of the zone $S_3$: S excluding $S_4$ and $S_5$ $$\begin{cases} 4x - y \geq 0 \\ z \geq 0.2 \\ x + y + z = 1 \end{cases}$$

with more particularly the following examples:

$x = 0.23 \quad y = 0.54 \quad z = 0.23 \quad T_\delta = +35.3_{2.7}$ $x = 0.33 \quad y = 0.34 \quad z = 0.33 \quad T_\delta = +35.7_{3.7}$ $x = 0.13 \quad y = 0.33 \quad z = 0.54 \quad T_\delta = +38.6_{2.6}$ $x = 0.70 \quad y = 0.28 \quad z = 0.02 \quad T_\delta = +30.8_{3.9}$ One zone where $4 < \delta \leq 6$: $S_4$
Definition of the zone $S_4$ $$\begin{cases} 2x + 7y - 3z \geq 0 \\ y \leq 0.3 \\ z \geq 0.4 \\ 9x - 6y - z \geq 0 \\ x + y + z = 1 \end{cases}$$

with more particularly the following example:

$x = 0.43 \quad y = 0.14 \quad z = 0.43 \quad T_\delta = +35.8_{5.1}$

Three zones where $\delta > 6$: $S_5$, $S_6$ and $S_7$
Definition of $S_5$:

$$\begin{cases} 2x + 7y - 3z < 0 \\ 9x - 6y - z \geq 0 \\ x + y + z = 1 \end{cases}$$

with more particularly the following examples:

$x = 0.48 \quad y = 0.02 \quad z = 0.50 \quad T_\delta = +36.3_{6.5}$ $x = 0.27 \quad y = 0.06 \quad z = 0.67 \quad T\delta = +39.2_{7.4}$ Definition of $S_6$ $$\begin{cases} x \geq 0.95 \\ x + y + z = 1 \end{cases}$$

Definition $S_7$ $$\begin{cases} 9x - y + 19z \leq 0 \\ x + y + z = 1 \end{cases}$$

Figure 6:
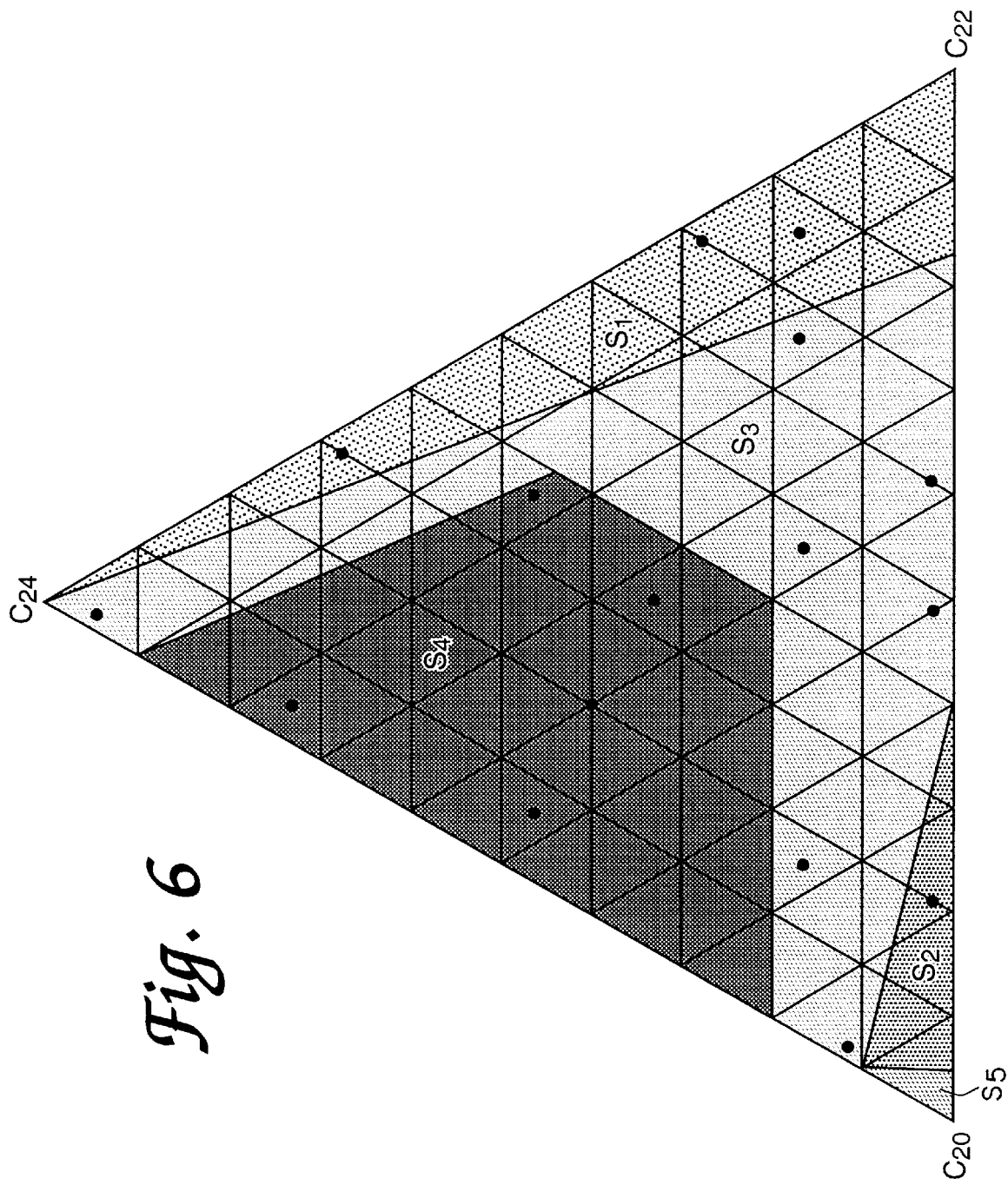

6: Study of the ternary ALCALs xC20-yC22-zC24
In the diagram showing the attributes of the different alloys (FIG. 6), five zones can be distinguished (surfaces numbered from $S_1$ to $S_5$).

Two zones where $\delta \leq 1$: $S_1$ and $S_2$
Definition of $S_1$:

$$\begin{cases} 5x - y \leq 0 \\ x + y + z = 1 \end{cases}$$

with more particularly the following examples:

$x = 0.02 \quad y = 0.30 \quad z = 0.68 \quad T_\delta = +48.1_{0.9}$ $x = 0.02 \quad y = 0.70 \quad z = 0.28 \quad T_\delta = +45.2_{0.8}$ $x = 0.07 \quad y = 0.76 \quad z = 0.17 \quad T_\delta = +44.7_{0.9}$ Definition of $S_2$:

$$\begin{cases} -2x + 3y + 18z \leq 0 \\ x + y + z = 1 \end{cases}$$

with more particularly the following examples:

$x = 0.78 \quad y = 0.20 \quad z = 0.02 \quad T_\delta = +38.0_{0.8}$

A zone where $1 \leq \delta < 2$: $S_3$
Definition of $S_3$ total triangle excluding $S_1$, $S_2$, $S_4$ and $S_5$
with more particularly the following examples:

$x = 0.05 \quad y = 0.02 \quad z = 0.93 \quad T_\delta = +50.5_{1.1}$ $x = 0.17 \quad y = 0.66 \quad z = 0.17 \quad T_\delta = +43.3_{1.2}$ $x = 0.37 \quad y = 0.46 \quad z = 0.17 \quad T_\delta = +42.0_{1.9}$ $x = 0.38 \quad y = 0.60 \quad z = 0.02 \quad T_\delta = +40.6_{1.4}$ $x = 0.50 \quad y = 0.48 \quad z = 0.02 \quad T_\delta = +40.0_{1.5}$ $x = 0.66 \quad y = 0.17 \quad z = 0.17 \quad T_\delta = +39.0_{1.6}$ $x = 0.87 \quad y = 0.02 \quad z = 0.11 \quad T_\delta = +38.6_{1.2}$ A zone where $2 < \delta \leq 4$: $S_4$
Definition of $S_4$:

$$\begin{cases} -36x + 9y + 4z \geq 0 \\ y \leq 0.4 \\ z \geq 0.2 \\ x + y + z = 1 \end{cases}$$

with more particularly the following examples:

$x = 0.23 \quad y = 0.03 \quad z = 0.74 \quad T_\delta = +47.0_{3.0}$ $x = 0.17 \quad y = 0.37 \quad z = 0.46 \quad T_\delta = +45.6_{2.2}$ $x = 0.47 \quad y = 0.06 \quad z = 0.47 \quad T_\delta = +43.4_{3.7}$ $x = 0.34 \quad y = 0.33 \quad z = 0.33 \quad T_\delta = +43.4_{2.8}$ $x = 0.40 \quad y = 0.20 \quad z = 0.40 \quad T_\delta = +43.3_{3.3}$ -continued $x = 0.66 \quad y = 0.07 \quad z = 0.27 \quad T_\delta = +39.9_{2.3}$ A zone where $\delta > 4$: $S_5$ Definition of $S_5$ $$\begin{cases} x - 19y - 9z \geq 0 \\ x + y + z = 1 \end{cases}$$

7: Study of the ternary ALCALs xC22-YC24-zC26

Figure 7:
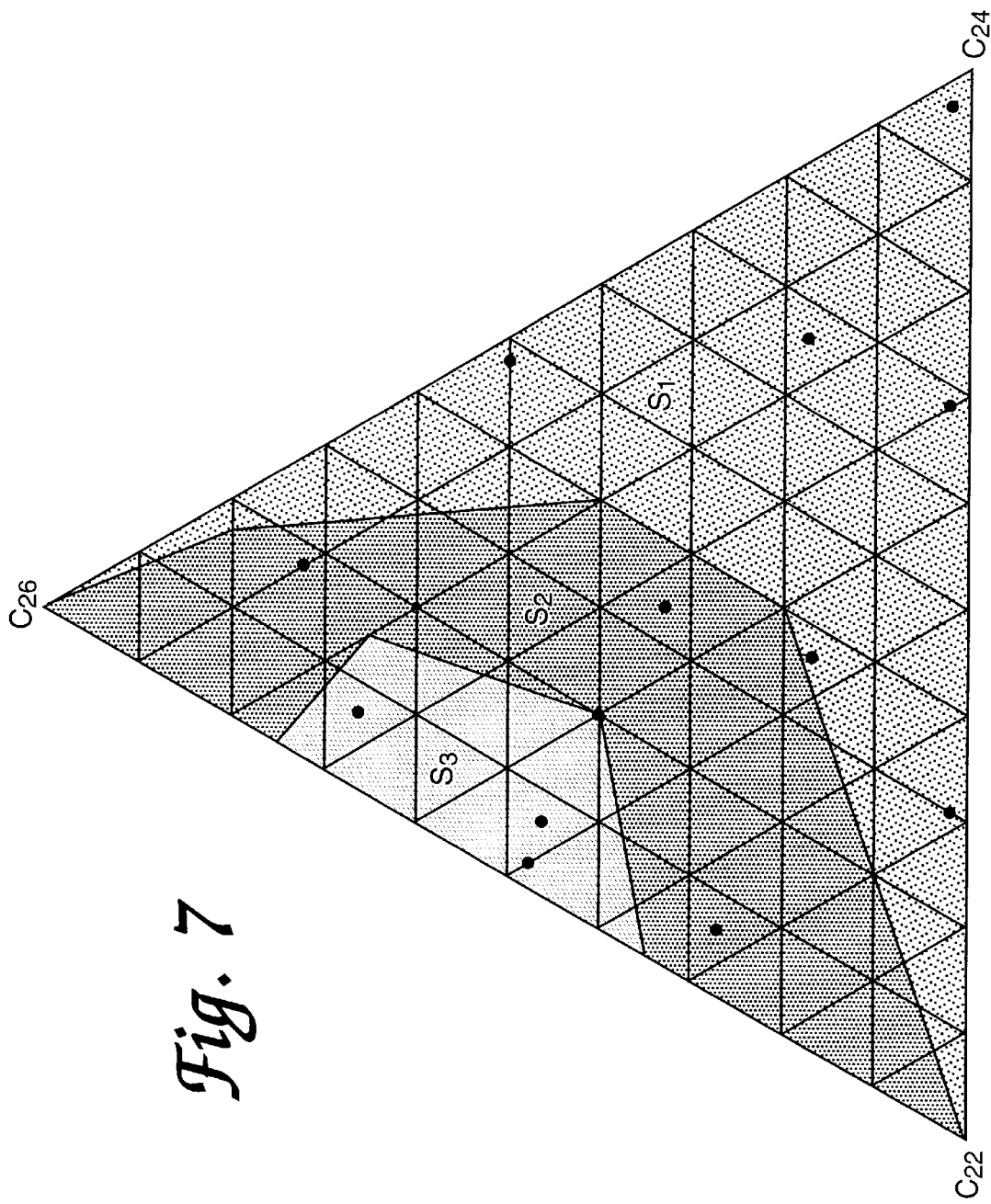

FIG. 7 is a diagram showing the attributes of the different alloys. Three zones can be distinguished (surfaces numbered from $S_1$ to $S_3$)

One zone where $\delta \leq 1$: $S_1$

Definition of $S_1$:

$$\begin{cases} 17x - 3y \leq 0 \\ y - 2z \geq 0 \\ 2x - 3y + 2z \leq 0 \\ 56x - 34y + 6z \leq 0 \\ x + y + z = 1 \end{cases}$$

with more particularly the following examples:

$x = 0.01 \quad y = 0.49 \quad z = 0.50 \quad T_\delta = +53.5_{0.9}$ $x = 0.03 \quad y = 0.95 \quad z = 0.02 \quad T_\delta = +50.5_{0.5}$ $x = 0.17 \quad y = 0.66 \quad z = 0.17 \quad T_\delta = +50.3_{0.8}$ $x = 0.30 \quad y = 0.68 \quad z = 0.02 \quad T_\delta = +48.6_{0.9}$ $x = 0.46 \quad y = 0.37 \quad z = 0.17 \quad T_\delta = +47.7_{1.1}$ $x = 0.68 \quad y = 0.30 \quad z = 0.02 \quad T_\delta = +45.7_{0.8}$ One zone where $1 < \delta \leq 2$: $S_2$ Definition of the zone $S_2$: total triangle excluding $S_1$ and $S_3$ with more particularly the following examples:

$x = 0.10 \quad y = 0.18 \quad z = 0.72 \quad T_\delta = +54.0_{1.9}$ $x = 0.66 \quad y = 0.07 \quad z = 0.27 \quad T_\delta = +47.2_{1.6}$ $x = 0.34 \quad y = 0.33 \quad z = 0.33 \quad T_\delta = +44.3_{1.4}$ One zone where $2 < \delta \leq 4$: $S_3$ Definition of $S_3$ $$\begin{cases} 12x + y - 4z \geq 0 \\ 7x - 18y + 2z \geq 0 \\ x + 2y - 2z \leq 0 \\ x + y + z = 1 \end{cases}$$

with more particularly the following examples:

$x = 0.27 \quad y = 0.07 \quad z = 0.66 \quad T_\delta = +52.2_{2.4}$

-continued $x = 0.50 \quad y = 0.01 \quad z = 0.49 \quad T_\delta = +50.2_{2.6}$ $x = 0.40 \quad y = 0.20 \quad z = 0.40 \quad T_\delta = +49.7_{2.1}$ $x = 0.47 \quad y = 0.06 \quad z = 0.47 \quad T_\delta = +49.8_{2.4}$ 8: Study of the ternary ALCALs xC20-yC22-zC26

Figure 8:
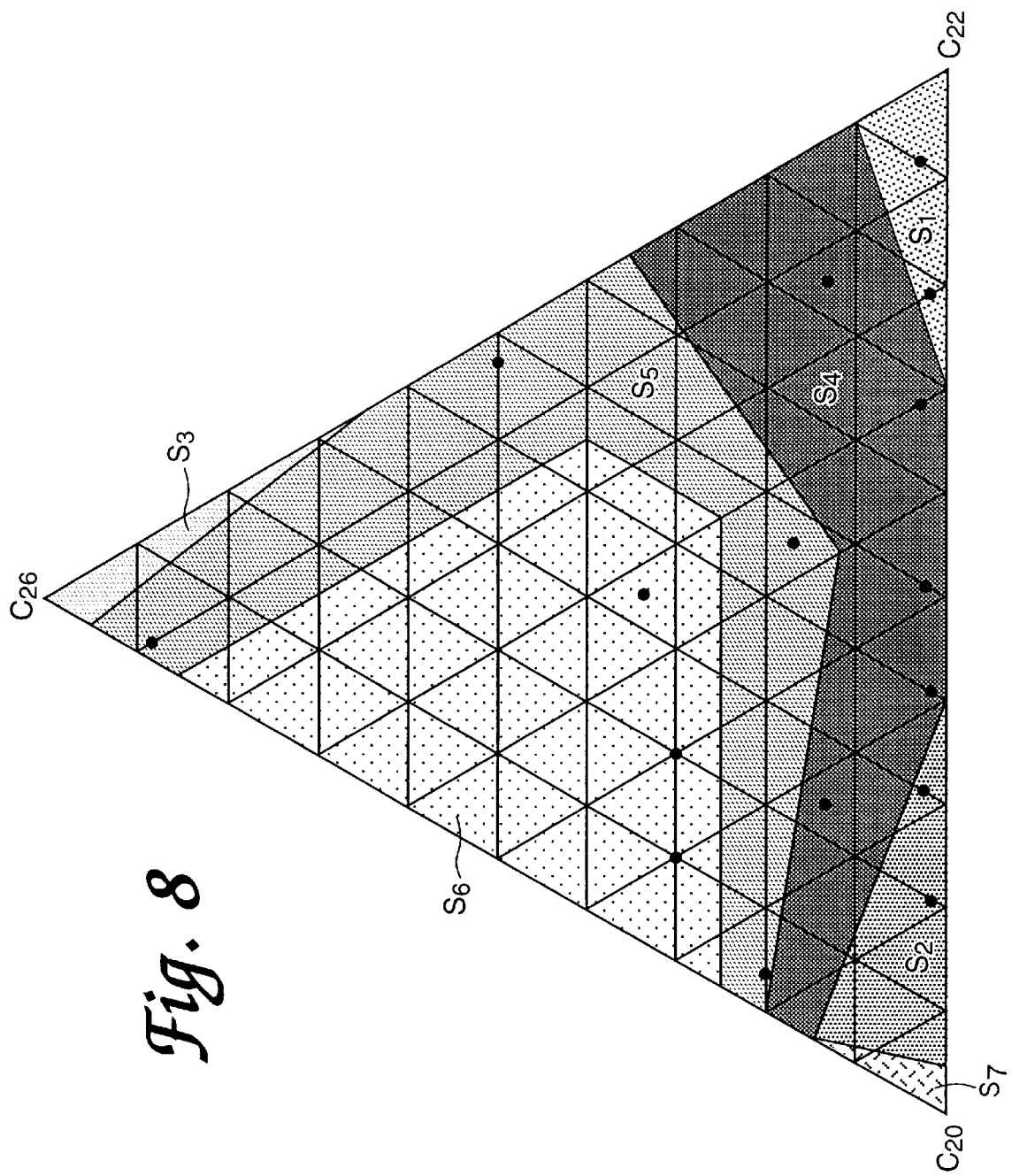

FIG. 8 is a diagram showing the attributes of the different alloys. Seven zones can be distinguished (surfaces numbered $S_1$ to $S_7$).

Two zones where $\delta \leq 1$: $S_1$ and $S_2$

Definition of the zone $S_1$ $$\begin{cases} 7x - 3y + 27z \leq 0 \\ x + y + z = 1 \end{cases}$$

with more particularly the following examples:

$x = 0.20 \quad y = 0.78 \quad z = 0.02 \quad T_\delta = +42.2_{0.9}$ $x = 0.07 \quad y = 0.90 \quad z = 0.03 \quad T_\delta = +43.3_{1.0}$ Definition of the zone $S_2$ $$\begin{cases} -6x + 3y + 17z \leq 0 \\ -3x + 57y + 17z > 0 \\ x + y + z = 1 \end{cases}$$

with more particularly the following examples:

$x = 0.78 \quad y = 0.20 \quad z = 0.02 \quad T_\delta = +37.8_{0.8}$ $x = 0.67 \quad y = 0.30 \quad z = 0.03 \quad T_\delta = +38.6_{0.9}$ Two zones where $1 < \delta \leq 2$: $S_3$ and $S_4$ Definition of $S_3$ $$\begin{cases} 119x + 13y - 7z \leq 0 \\ x + y + z = 1 \end{cases}$$

Definition of $S_4$: S excluding $S_1$, $S_2$ and $S_7$ $$\begin{cases} 6x + y - 24z \geq 0 \\ 14x - 21y + 39z \leq 0 \\ x + y + z = 1 \end{cases}$$

with more particularly the following examples:

$x = 0.63 \quad y = 0.23 \quad z = 0.14 \quad T_\delta = +39.5_{1.8}$ $x = 0.58 \quad y = 0.40 \quad z = 0.02 \quad T_\delta = +39.1_{1.1}$ $x = 0.47 \quad y = 0.50 \quad z = 0.03 \quad T_\delta = +40.4_{1.5}$ $x = 0.30 \quad y = 0.67 \quad z = 0.03 \quad T_\delta = +41.8_{1.4}$ -continued $x = 0.13 \quad y = 0.74 \quad z = 0.13 \quad T_\delta = +43.8_{1.5}$ One zone where $2<\delta\leq 4$: $S_5 = S$ not including $S_6$
Definition of $S_5$: S excluding $S_6$ $$\begin{cases} 6x + y - 24z > 0 \\ 14x - 21y + 39z > 0 \\ 119x + 13y - 7z < 0 \\ x + y + z = 1 \end{cases}$$

with more particularly the following examples:

$x = 0.03 \quad y = 0.47 \quad z = 0.50 \quad T_\delta = +50.0_{3.5}$ $x = 0.37 \quad y = 0.46 \quad z = 0.17 \quad T_\delta = +42.6_{2.6}$ $x = 0.77 \quad y = 0.03 \quad z = 0.20 \quad T_\delta = +38.8_{2.1}$ $x = 0.10 \quad y = 0.02 \quad z = 0.88 \quad T_\delta = +54.5_{3.7}$ Two zones where $\delta \leq 6$: $S_6$ and $S_7$
Definition of $S_6$ $$\begin{cases} x \geq 0.15 \\ y \leq 0.45 \\ z \geq 0.25 \\ x + y + z = 1 \end{cases}$$

with more particularly the following example:

$x = 0.33 \quad y = 0.34 \quad z = 0.33 \quad T_\delta = +46.6_{6.0}$

Definition of $S_7$ $$\begin{cases} -3x + 57y + 17z \leq 0 \\ x + y + z = 1 \end{cases}$$

9: Study of the ternary ALCALs xC44-yC46-zC50
In the diagram showing the attributes of the different alloys (FIG. 9) two zones can be distingushed (surfaces numbered from $S_1$ to $S_2$).
One zone where $\delta \leq 1$: $S_1$
Definition of $S_1$ Total triangle not including $S_2$ with more particularly the following examples:

$x = 0.78 \quad y = 0.02 \quad z = 0.20 \quad T_\delta = +86.7_{0.7}$ $x = 0.40 \quad y = 0.40 \quad z = 0.20 \quad T_\delta = +87.2_{0.5}$ One zone where $1<\delta\leq 2$: $S_2$
Definition of $S_2$ $$\begin{cases} x \geq 0.25 \\ y \leq 0.15 \\ z \geq 0.35 \\ x + y + z = 1 \end{cases}$$

with more particularly the following example:

$x = 0.40 \quad y = 0.02 \quad z = 0.58 \quad T_\delta = +89.2_{1.5}$

EXAMPLE 6
Quaternary and higher ALCALs

The same considerations concerning the various $\epsilon_n$s of the constituents taken in pairs enable multi-component ALCALs to be produced which are acceptable as regards their attribute $\delta$.
Examples of formulations $C14_{0.330}C15_{0.390}C16_{0.140}C18_{0.140}$: T=+7.5° C. $\delta$=3.4. $\Delta H$=127 J/g $C14_{0.290}C15_{0.350}C16_{0.130}C17_{0.230}$: T=+8.6° C. $\delta$=4.0. $\Delta H$=146 J/g $C44_{0.350}C46_{0.350}C48_{0.100}C50_{0.200}$: T=+86.9° C. $\delta$=0.6. $\Delta H$=220 J/g $C14_{0.300}C15_{0.360}C16_{0.140}C17_{0.060}C18_{0.140}$: T=+7.6° C., $\delta$=3.5, $\Delta H$=128 J/g

EXAMPLE 7
Molecular alloys formed by monoacid-monoacid chains: the following results were obtained with the formulation $[CH_3(CH_2)_{18}COOH]_{0.52}[CH_3(CH_2)_{20}COOH]_{0.48}$: T=+69.7° C., $\delta$=0.9, $\Delta H$=204 J/g

EXAMPLE 8
Molecular alloys formed by alcane-diacid chains: with the following formulation $[C_{22}H_{46}]_{0.80}[COOH(CH_2)_{20}COOH]_{0.20}$, we obtain: T=+44.3° C., $\delta$=1.7, $\Delta H$=188 J/g

EXAMPLE 9
Molecular alloys formed by monoacid-diacid chains
An advantageous eutectic mixture of alloys corresponds to the following global composition:
0.94 of $[CH_3(CH_2)_{20}COOH]$ with
0.06 of $[COOH(CH_2)_{20}COOH]$
T=+77.2° C., $\delta$=0, et $\Delta H$=160 J/g

EXAMPLE 10
Application to the production of trays for market fish stall displays A display of trays containing ALCALs with attribute $\delta \leq 4$. was covered. In comparison with the ice at present used, the trays had the advantage that they could be regenerated by cooling. If necessary they could be used under a small thickness of ice, which will be better preserved if the traditional presentation is desired.

EXAMPLE 11
Application to the cold preservation of a transported foodstuff

Let us suppose that a solid or liquid foodstuff which is to be preserved in its packaging in a conventional refrigerator is to be transported to a given place (for example, a work site or picnic area), for consumption several hours later without any other means of protection and without its temperature exceeding 13° C. (for example). Advantageously, one of the ALCALs appearing in the following list of formulations will be selected. The selection is wide open; it will be made in dependence on the parameters to be given precedence, more particularly on economic constraints and the availability of the base products:

|  | T (° C.) | δ (° C.) | ΔHJ · g$^{-1}$ |
|---|---|---|---|
| $C14_{0.214}C15_{0.561}C16_{0.225}$ | +8.5 | 2.3 | 152 |
| $C14_{0.290}C15_{0.350}C16_{0.130}C17_{0.220}C18_{0.010}$ | +8.6 | 4.1 | 146 |
| $C14_{0.320}C15_{0.240}C16_{0.440}$ | +8.8 | 4.4 | 151 |
| $C14_{0.400}C16_{0.600}$ | +9.0 | 4.9 | 148 |
| $C14_{0.107}C15_{0.592}C16_{0.220}C17_{0.059}C18_{0.022}$ | +9.4 | 2.3 | 145 |
| $C14_{0.030}C15_{0.840}C16_{0.130}$ | +9.5 | 1.0 | 153 |
| $C14_{0.240}C15_{0.330}C16_{0.430}$ | +9.5 | 3.9 | 151 |
| $C14_{0.330}C15_{0.070}C16_{0.600}$ | +9.9 | 4.4 | 151 |
| $C15_{0.870}C16_{0.070}C17_{0.060}$ | +10.3 | 1.0 | 158 |
| $C14_{0.010}C15_{0.840}C16_{0.150}$ | +10.5 | 0.8 | 150 |
| $C14_{0.030}C15_{0.640}C16_{0.330}$ | +10.7 | 2.0 | 152 |
| $C14_{0.066}C15_{0.505}C16_{0.369}$ | +10.7 | 2.1 | 158 |
| $C15_{0.770}C16_{0.170}C17_{0.060}$ | +10.8 | 1.3 | 157 |
| $C15_{0.770}C16_{0.070}C17_{0.160}$ | +10.9 | 1.4 | 154 |
| $C15_{0.700}C16_{0.300}$ | +11.2 | 1.3 | 156 |
| $C15_{0.660}C16_{0.250}C17_{0.070}C18_{0.030}$ | +11.2 | 1.9 | 152 |
| $C15_{0.700}C17_{0.300}$ | +11.3 | 1.3 | 146 |
| $C15_{0.685}C17_{0.300}C16_{0.015}$ | +11.3 | 1.3 | 146 |
| $C15_{0.670}C16_{0.300}C17_{0.030}$ | +11.4 | 1.4 | 155 |
| $C14_{0.140}C15_{0.230}C16_{0.630}$ | +11.9 | 3.1 | 147 |

By way of example, if the first alloy in this list is chosen, a PCMMA will be available which can be stored with 95% efficiency between +6.2° C. and +8.5° C. Clearly, a man skilled in the art can readily devise other suitable formulations.

It is sufficient to produce a double-walled packaging (completely enclosing the foodstuff), between which the ALCAL will be placed; the thickness of ALCAL to be used will depend on the required protection period. When the whole is placed in the refrigerator, the ALCAL will solidify (since the temperature therein is lower than its $T_{sol}$) and the whole will take on the temperature of the place in the refrigerator where it is positioned. During transport of the whole at ambient temperature, the ALCAL will form a barrier against the access of heat to the actual foodstuff, since the heat coming from outside will first be absorbed by the ALCAL to raise its temperature to $T_{sol}$. Then all the heat will be taken by the ALCAL for its melting, and it is the ΔH.m energy which will thus be blocked by the PCMMA (if m is its mass). The temperature of the whole will rise above $T_{liq}$ only when all the ALCAL has melted.

EXAMPLE 12
Application to cooling packings and heating covers

A layer of ALCAL is incorporated on the packing or the cover. In the former case the ALCAL is so selected that its operating temperature is of the order of +35° C. A stay in a cool room is enough to give the system its properties—i.e., to make the ALCAL solid. The patient will therefore remain in contact with the surface at +35° C. as long as the heat which it gives off is not enough to make all the PCMMA melt.

In the second case the use of a heating resistance can be envisaged for the storage of energy—i.e., to make an ALCAL melt which operates at +38° C., for example, with δ≦2; use is then possible without the usual risks of heating covers, since the power is disconnected. Maintenance between +38° C. and +(38−δ)°C. will persist until the PCMMA has completed its transition.

EXAMPLE 13
Heating mattress for operating tables and treatment tables

Certain long lasting operations require assistance to the patient in the form of heat provided to compensate for hypothermia. The operating principal of the heating cover (ALCAL with T=+38° C. and δ≦2, with incorporated resistance) can be adopted by associating therewith a low voltage system (for example, a battery) associated with a cyclic contactor to maintain the ALCAL in solid-liquid equilibrium during a long lasting operation or during the transport of a patient. In this example, PCMMAs can be associated with other materials, such as fibrous or expanded materials, for reasons of comfort. Heat insulating layers on the external surfaces (not in contact with the patient) will prolong autonomy of operation.

EXAMPLE 14
Fondue

A system is produced which has an incorporated resistance and operates with power disconnected with a PCMMA (at a T higher than +100° C. and with a δ≦4) placed in a double wall. The resulting apparatus thus ensures high safety in its operation. The PCMMAs can advantageously be selected from the long-chain diacids.

EXAMPLE 15
Cyclist's flask

A double-walled flask was produced containing an ALCAL with δ≦4° C. operating at a temperature of the order of +15° C. (or even lower, as required); the cyclist will therefore have a refreshing drink for several hours, this being a great advantage in comparison with conventional flasks.

EXAMPLE 16
Case for vaccines

A double-walled case is prepared into which a PCMMA is introduced of temperature T lower than approximately 15° C. with δ≦4. The PCMMA is solidified by placing it in a refrigerator. The case can be used for transporting a vaccine.

This application is very advantageous, for example, to ramblers who have, for example, an anti-viper vaccine, so that they can make their trip with improved safety.

The invention will therefore provide the means for producing PCMs corresponding to a wide range of temperatures required for industrial applications.

In relation to the temperature level at which the phase change must take place, a man skilled in the art is provided with the means of selecting the content of the organic compounds used to produce the alloy in conformity with the requirements defined hereinbefore.

We claim:

1. A composition for storing and restoring thermal energy by latent heat consisting of one single phase of acyclic organic compounds which at the solid state is a solid solution of substitution, characterized as such by X rays, and having formula (I):

$$A_{x_a}Z_{x_z} \qquad (I)$$

wherein

A and Z are different, and each represents an optionally substituted alkane having from 8 to 120 carbon atoms, $x_a$ and $x_z$ denote the molar proportions of A and Z respectively, said proportions being adjusted to obtain an alloy having one or more transitions at one or more levels of temperature T such as required for a given application, over a temperature range δ not exceeding +6° C.

2. A composition according to claim 1, wherein δ does not exceed +4° C.

3. A composition according to claim 2, wherein δ does not exceed +2° C.

4. A composition according to claim 1, wherein at least one of A or Z contains one or more substituents selected from the group consisting of F, Cl, Br, or I; —OH; —OR$_1$ groups; C$_1$-C$_4$ alkyl, C$_1$-C$_4$ alkylene, C$_1$-C$_4$ alkyne; —COOH, —COOR$_1$, —COR$_1$, —CH$_2$OH, —CH(R$_1$)—OH, —C(R$_1$, R$_2$)OH, or their ethers; —CHO, —C=O, —CONH$_2$, —NH$_2$, —NH(R$_1$), or —N(R$_1$, R$_2$); —SH, =S, and —NO$_2$, wherein R$_1$ and R$_2$ are identical or different and are selected from the group consisting of an alkyl group having 1 to 8 carbon atoms, an amine group, a ketone group, a sulfhydryl group, and an amide group.

5. A composition according to claim 1, wherein A and Z have an even number of carbon atoms.

6. A composition according to claim 1, wherein said composition contains at least one alloy represented by the following formulae: A$_{xa}$ B$_{xb}$ (II), A$_{xa}$ B$_{xb}$ C$_{xc}$ (III), or A$_{xa}$ B$_{xb}$ C$_{xc}$ D$_{xd}$ (IV), in which A, B, C and D are different and each represent a substituted or unsubstituted acyclic alkane having 8–120 carbon atoms, and x$_a$ to x$_d$ correspond to the molar proportions of the various constituents respectively, wherein x$_a$+x$_b$=1 in formula (II), x$_a$+x$_b$+x$_c$=1 in formula (III) and x$_a$+x$_b$+x$_c$+x$_d$=1 in formula (IV).

7. A composition according to claim 1, wherein δ does not exceed +1° C.

8. A composition according to claim 1, wherein A and Z have an odd number of carbon atoms.

9. A composition according to claim 1, wherein one of A and Z has an even number of carbon atoms and the other has an odd number of carbon atoms.

10. A composition according to claim 1, wherein said acyclic compound comprises at least one alkyl chain having at least one substituent selected from the group consisting of carboxyl, ester, and halogen.

11. A composition according to claim 1, wherein A and Z are alkyl chains which are consecutive.

12. A composition according to claim 1, wherein A and Z are alkyl chains of differing lengths.

13. The composition of claim 1, wherein A and Z are miscible in all proportions prior to the transition.

14. The composition of claim 1, wherein A and Z form an eutectic.

15. A composition for storing and restoring thermal energy by latent heat consisting of one single phase of acyclic organic compounds which at the solid state is a solid solution of substitution, characterized as such by X rays, and having formula (I):

$$A_{x_a} Z_{x_z} \quad (I)$$

wherein

A and Z are different, and each represents an alkane having from 8 to 50 carbon atoms, x$_a$ and x$_z$ denote the molar proportions of A and Z respectively, said proportions being adjusted to obtain an alloy having one or more transitions at one or more levels of temperature T such as required for a given application, over a temperature range δ not exceeding +6° C.

16. A process for the preparation of a composition according to claim 1, which comprises providing starting compounds A and Z in the respective proportions required in the final molecular alloy to obtain a mixture and subjecting said mixture to a process selected from the group consisting of mixing and agitation; melting and crystallization; melting and quenching; dissolution and evaporation; simultaneous sublimation; zone levelling; or chemical interdiffusion.

17. The process according to claim 15, wherein A and Z are short chain alkanes which are liquid at ambient temperature, and said alloy is obtained by mixing and agitating A and Z in the proportions required in the molecular alloy to form a liquid solution thereof.

18. The process according to claim 15, wherein when some or all of the starting compounds are solid, the starting compounds are dissolved in suitable proportions in a mutual solvent, whereafter the solvent is evaporated.

19. The process according to claim 15, wherein the process further comprises melting products with agitation to ensure the homogeneity of the product, and quenching the melted and agitated product.

20. The process according to claim 15, wherein the process further comprises subjecting a mixture of compound A and compound Z to an extraction step whereby the composition is isolated, and, optionally, treating the extracted composition to adjust the concentration of at least one of compounds A or Z.

21. A packaging comprised of phase change material containing a composition according to claim 1.

22. A method for making a composition for maintaining an article within a limited temperature range, said composition being formed by one or more molecular alloys each consisting of one single phase of acyclic alkanes which at the solid state is a solid solution of substitution, characterized as such by X rays, and having formula (I):

$$A_{x_a} Z_{x_z} \quad (I)$$

wherein

A and Z are different, and each represents an optionally substituted alkane having from 8 to 120 carbon atoms, having the latent heat conventionally required to be a phase change material, x$_a$ and x$_z$ denote the molar proportions of A and Z respectively, said method comprising combining A and Z in proportions x$_a$ and x$_z$, said proportions being selected so that the compounds, for each molecular alloy, are totally miscible prior to the phase transition, and in the case of invariance levels, the proportions are are selected so that the concentrations of the compounds are outside said invariance levels to obtain an alloy having a transition at a temperature T which occurs over a temperature range δ not exceeding +6° C.

* * * * *